United States Patent
Shin et al.

(10) Patent No.: US 12,377,132 B2
(45) Date of Patent: *Aug. 5, 2025

(54) METHOD FOR TREATING OR SENSITIZING INTERFERON BETA RESISTANT CANCER COMPRISING CFLIP SIRNA

(71) Applicants: ABION INC., Seoul (KR); SEOUL NATIONAL UNIVERSITY R&DB FOUNDATION, Seoul (KR)

(72) Inventors: Young Kee Shin, Seoul (KR); Tae Eun Kim, Anyang-si (KR); Sung Youl Hong, Incheon (KR); Jun Young Choi, Gwangmyeong-si (KR); Na Young Kim, Anyang-si (KR)

(73) Assignees: SEOUL NATIONAL UNIVERSITY R&DB FOUNDATION, Seoul (KR); ABION INC., Seoul (KR)

( * ) Notice: Subject to any disclaimer, the term of this patent is extended or adjusted under 35 U.S.C. 154(b) by 429 days.

This patent is subject to a terminal disclaimer.

(21) Appl. No.: 17/898,317

(22) Filed: Aug. 29, 2022

(65) Prior Publication Data

US 2023/0241176 A1     Aug. 3, 2023

Related U.S. Application Data

(63) Continuation of application No. 16/321,409, filed as application No. PCT/KR2017/008239 on Jul. 31, 2017, now Pat. No. 11,464,832.

(30) Foreign Application Priority Data

Jul. 29, 2016   (KR) .................. 10-2016-0097516

(51) Int. Cl.
| | |
|---|---|
| A61K 38/21 | (2006.01) |
| A61K 31/713 | (2006.01) |
| A61K 39/00 | (2006.01) |
| A61P 35/00 | (2006.01) |

(52) U.S. Cl.
CPC .......... *A61K 38/215* (2013.01); *A61K 31/713* (2013.01); *A61K 39/00* (2013.01); *A61P 35/00* (2018.01)

(58) Field of Classification Search
CPC .. A61K 38/215; A61K 31/713; C07K 14/565; C12N 2310/14
See application file for complete search history.

(56) References Cited

U.S. PATENT DOCUMENTS

| 2004/0126791 A1 | 7/2004 | Wajant et al. |
| 2012/0082647 A1 | 4/2012 | Baker et al. |

FOREIGN PATENT DOCUMENTS

| JP | 2007513611 A | 5/2007 |
| JP | 2008518631 A | 6/2008 |
| KR | 10-2006-003913 A | 5/2006 |

OTHER PUBLICATIONS

Apelbaum et al., "Type I Interferons Induce Apoptosis by Balancing cFLIP and Caspase-8 Independent of Death Ligands", Molecular and Cellular Biology, 2013, 33(4): 800-814.
NCBI, Genbank accession No. BAN63131.1, (Jul. 17, 2013).
NCBI, Genbank accession No. U97074.1 (Jul. 15, 1997).
Ogasawara et al., "Growth Inhibitory Effects of IFN-B on Human Liver Cancer Cells In Vitro and In Vivo", Journal of Interferon & Cytokine Research, 2007, 27:507-516.
Jaitin et al., "Inquiring into the Differential Action of Interferons (IFNs): an IFN-α2 Mutant with Enhanced Affinity to IFNAR1 Is Functionally Similar to IFN-β", Molecular and Cellular Biology, Mar. 2006, 26(5): 1888-1897.
Kim et al., "Sensitization of glycoengineered interferon-β1a-resistant cancer cells by cFLIP inhibition for enhanced anti-cancer therapy", Oncotarget, 2017, 8(8): 13957-13970.
Lee et al., "A Glycoengineered Interferon-β Mutein (R27T) Generates Prolonged Signaling by an Altered Receptor-Binding Kinetics", Frontiers in Pharmacology, Jan. 2019, vol. 9, Article 1568, 13 pages.

*Primary Examiner* — Elly-Gerald Stoica
(74) *Attorney, Agent, or Firm* — James S. Keddie; Bozicevic, Field & Francis LLP

(57) ABSTRACT

The present invention relates to a composition for treating or sensitizing interferon beta resistant cancer disease comprising cFLIP siRNA, and, more specifically, to a pharmaceutical composition for treating interferon beta resistant cancer disease, comprising, as an active ingredient: (a) an siRNA complementarily binding to mRNA of a cFLIP gene; and (b) a human interferon beta variant which comprises glycine-asparagine-isoleucine-threonine-valine sequence (GNITV) at C-terminus in a human natural interferon beta amino acid sequence shown in SEQ ID NO: 1, or has replaced the 27$^{th}$ arginine amino acid with threonine or serine.

10 Claims, 8 Drawing Sheets
Specification includes a Sequence Listing.

SEQUENCE LISTING

```
Sequence total quantity: 33
SEQ ID NO: 1                moltype = AA  length = 166
FEATURE                     Location/Qualifiers
source                      1..166
                            mol_type = protein
                            organism = synthetic construct
SEQUENCE: 1
MSYNLLGFLQ RSSNFQCQKL LWQLNGRLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRN                  166

SEQ ID NO: 2                moltype = AA  length = 166
FEATURE                     Location/Qualifiers
source                      1..166
                            mol_type = protein
                            organism = synthetic construct
SEQUENCE: 2
MSYNLLGFLQ RSSNFQCQKL LWQLNGTLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRN                  166

SEQ ID NO: 3                moltype = AA  length = 166
FEATURE                     Location/Qualifiers
source                      1..166
                            mol_type = protein
                            organism = synthetic construct
SEQUENCE: 3
MSYNLLGFLQ RSSNFQCQKL LWQLNGSLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRN                  166

SEQ ID NO: 4                moltype = AA  length = 171
FEATURE                     Location/Qualifiers
source                      1..171
                            mol_type = protein
                            organism = synthetic construct
SEQUENCE: 4
MSYNLLGFLQ RSSNFQCQKL LWQLNGRLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRNGNIT V            171

SEQ ID NO: 5                moltype = AA  length = 171
FEATURE                     Location/Qualifiers
source                      1..171
                            mol_type = protein
                            organism = synthetic construct
SEQUENCE: 5
MSYNLLGFLQ RSSNFQCQKL LWQLNGTLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRNGNIT V            171

SEQ ID NO: 6                moltype = AA  length = 171
FEATURE                     Location/Qualifiers
source                      1..171
                            mol_type = protein
                            organism = synthetic construct
SEQUENCE: 6
MSYNLLGFLQ RSSNFQCQKL LWQLNGSLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRNGNIT V            171

SEQ ID NO: 7                moltype = DNA  length = 1443
FEATURE                     Location/Qualifiers
source                      1..1443
                            mol_type = other DNA
                            organism = synthetic construct
SEQUENCE: 7
atgtctgctg aagtcatcca tcaggttgaa gaagcacttg atacagatga aaggagatg     60
ctgctctttt tgtgccggga tgttgctata gatgtggttc cacctaatgt cagggacctt   120
ctggatattt tacgggaaag aggtaagctg tctgtcgggg acttggctga actgctctac   180
agagtgaggc gatttgacct gctcaaacgt atcttgaaga tggacagaaa agctgtggag   240
acccaccctgc tcaggaaccc tcaccttgtt tcggactata gagtgctgat ggcagagatt   300
ggtgaggatt tggataaatc tgatgtgtcc tcattaattt tcctcatgaa ggattacatg   360
ggccgaggca agataagcaa ggagaagagt ttcttggacc ttgtggttga gttggagaaa   420
ctaaatctgg ttgccccaga tcaactggat ttattagaaa aatgcctaaa gaacatccac   480
agaatagacc tgaagacaaa aatccagaag tacaagcagt ctgttcaagg agcagggaca   540
agttacagga atgttctcca agcagcaatc caaaagagtc tcaaggatcc ttcaaataac   600
ttcaggctcc ataatgggag aagtaaagaa caaagactta ggaacagct tggcgctcaa   660
```

```
                                           -continued
caagaaccag tgaagaaatc cattcaggaa tcagaagctt ttttgcctca gagcatacct    720
gaagagagat acaagatgaa gagcaagccc ctaggaatct gcctgataat cgattgcatt    780
ggcaatgaga cagagcttct tcgagacacc ttcacttccc tgggctatga agtccagaaa    840
ttcttgcatc tcagtatgca tggtatatcc cagattcttg ccaatttgc ctgtatgccc     900
gagcaccgag actacgacag cttttgtgtgt gtcctggtga gcgaggagg ctcccagagt    960
gtgtatggtg tggatcagac tcactcaggg ctccccctgc atcacatcag gaggatgttc   1020
atgggagatt catgcccta tctagcaggg aagccaaaga tgttttttat tcagaactat   1080
gtggtgtcag agggccagct ggaggacagc agcctcttgg aggtggatgg ccagcgatg   1140
aagaatgtgg aattcaaggc tcagaagcga gggctgtgca cagttcaccg agaagctgac   1200
ttcttctgga gcctgtgtac tgcggacatg tccctgctgg agcagtctca cagctcacca   1260
tccctgtacc tgcagtgcct ctcccagaaa ctgagacaag aaagaaaacg cccactcctg   1320
gatcttcaca ttgaactcaa tggctacatg tatgattgga cagcagagt ttctgccaag   1380
gagaaatatt atgtctggct gcagcacact ctgagaaaga aacttatcct ctcctacaca   1440
taa                                                                 1443

SEQ ID NO: 8            moltype = DNA    length = 666
FEATURE                 Location/Qualifiers
source                  1..666
                        mol_type = other DNA
                        organism = synthetic construct
SEQUENCE: 8
atgtctgctg aagtcatcca tcaggttgaa gaagcacttg atacagatga gaaggagatg     60
ctgctctttt tgtgccggga tgttgctata gatgtggttc cacctaatgt cagggacctt   120
ctggatattt tacgggaaag aggtaagctg tctgtcgggg acttggctga actgctctac   180
agagtgaggc gatttgacct gctcaaacgt atcttgaaga tggacagaaa agctgtggag   240
acccacctgc tcaggaaccc tcaccttgtt tcggactata gagtgctgat ggcagagatt   300
ggtgaggatt tggataaatc tgatgtgtcc tcattaattt tcctcatgaa ggattacatg   360
ggccgaggca agataagcaa ggagaagagt ttccttggacc ttgtggttga gttgagaaa   420
ctaaatctgt tgccccaga tcaactggat ttattagaaa aatgcctaaa gaacatccac    480
agaatagacc tgaagacaaa aatccagaag tacaagcagt ctgttcaagg agcagggaca   540
agttacagga atgttctcca agcagcaatc caaaagagtc tcaaggatcc ttcaaataac   600
ttcaggatga taacacccta tgcccattgt cctgatctga aaattcttgg aaattgttcc   660
atgtga                                                              666

SEQ ID NO: 9            moltype = RNA    length = 21
FEATURE                 Location/Qualifiers
source                  1..21
                        mol_type = other RNA
                        organism = synthetic construct
SEQUENCE: 9
cttgaagatg gacagaaaag c                                              21

SEQ ID NO: 10           moltype = RNA    length = 21
FEATURE                 Location/Qualifiers
source                  1..21
                        mol_type = other RNA
                        organism = synthetic construct
SEQUENCE: 10
ccttgtttcg gactatagag t                                              21

SEQ ID NO: 11           moltype = RNA    length = 21
FEATURE                 Location/Qualifiers
source                  1..21
                        mol_type = other RNA
                        organism = synthetic construct
SEQUENCE: 11
gttgagttgg agaaactaaa t                                              21

SEQ ID NO: 12           moltype = RNA    length = 21
FEATURE                 Location/Qualifiers
source                  1..21
                        mol_type = other RNA
                        organism = synthetic construct
SEQUENCE: 12
gaatagacct gaagacaaaa a                                              21

SEQ ID NO: 13           moltype = RNA    length = 19
FEATURE                 Location/Qualifiers
source                  1..19
                        mol_type = other RNA
                        organism = synthetic construct
SEQUENCE: 13
caagcagtct gttcaagga                                                 19

SEQ ID NO: 14           moltype = RNA    length = 21
FEATURE                 Location/Qualifiers
source                  1..21
                        mol_type = other RNA
                        organism = synthetic construct
```

```
SEQUENCE: 14
gttgaagaag cacttgatac a                                                      21

SEQ ID NO: 15           moltype = RNA  length = 19
FEATURE                 Location/Qualifiers
source                  1..19
                        mol_type = other RNA
                        organism = synthetic construct
SEQUENCE: 15
gtgccgggat gttgctata                                                         19

SEQ ID NO: 16           moltype = RNA  length = 21
FEATURE                 Location/Qualifiers
source                  1..21
                        mol_type = other RNA
                        organism = synthetic construct
SEQUENCE: 16
cagatcaact ggatttatta g                                                      21

SEQ ID NO: 17           moltype = RNA  length = 21
FEATURE                 Location/Qualifiers
source                  1..21
                        mol_type = other RNA
                        organism = synthetic construct
SEQUENCE: 17
caaaaatcca gaagtacaag c                                                      21

SEQ ID NO: 18           moltype = AA  length = 627
FEATURE                 Location/Qualifiers
source                  1..627
                        mol_type = protein
                        organism = synthetic construct
SEQUENCE: 18
EVQLLESGGG LVQPGGSLRL SCAASGFTFS GYYMSWVRQA PGKGLEWVSV ISHDGSSTYY             60
ADSVKGRFTI SRDNSKNTLY LQMNSLRAED TAVYYCAKDA RVCTPKRCYS YDAMDVWGQG            120
TLVTVSSAST KGPSVFPLAP SSKSTSGGTA ALGCLVKDYF PEPVTVSWNS GALTSGVHTF            180
PAVLQSSGLY SLSSVVTVPS SSLGTQTYIC NVNHKPSNTK VDKKVEPKSC DKTHTCPPCP            240
APELLGGPSV FLFPPKPKDT LMISRTPEVT CVVVDVSHED PEVKFNWYVD GVEVHNAKTK            300
PREEQYNSTY RVVSVLTVLH QDWLNGKEYK CKVSNKALPA PIEKTISKAK GQPREPQVYT            360
LPPSRDELTK NQVSLTCLVK GFYPSDIAVE WESNGQPENN YKTTPPVLDS DGSFFLYSKL            420
TVDKSRWQQG NVFSCSVMHE ALHNHYTQKS LSLSPGKGGG GSSYNLLGFL QRSSNFQCQK            480
LLWQLNGTLE YCLKDRMNFD IPEEIKQLQQ FQKEDAALTI YEMLQNIFAI FRQDSSSTGW            540
NETIVENLLA NVYHQINHLK TVLEEKLEKE DFTRGKLMSS LHLKRYYGRI LHYLKAKEYS            600
HCAWTIVRVE ILRNFYFINR LTGYLRN                                                627

SEQ ID NO: 19           moltype = AA  length = 386
FEATURE                 Location/Qualifiers
source                  1..386
                        mol_type = protein
                        organism = synthetic construct
SEQUENCE: 19
QSVLTQPPSA SGTPGQRVTI SCTGSSSNIG SNAVTWYQQL PGTAPKLLIY ADSHRPSGVP             60
DRFSGSKSGT SASLAISGLR SEDEADYYCG AWDDSLNAYV FGGGTKLTVL GQPKAAPSVT            120
LFPPSSEELQ ANKATLVCLI SDFYPGAVTV AWKADSSPVK AGVETTTPSK QSNNKYAASS            180
YLSLTPEQWK SHKSYSCQVT HEGSTVEKTV APAECSGGGG SSYNLLGFLQ RSSNFQCQKL            240
LWQLNGTLEY CLKDRMNFDI PEEIKQLQQF QKEDAALTIY EMLQNIFAIF RQDSSSTGWN            300
ETIVENLLAN VYHQINHLKT VLEEKLEKED FTRGKLMSSL HLKRYYGRIL HYLKAKEYSH            360
CAWTIVRVEI LRNFYFINRL TGYLRN                                                 386

SEQ ID NO: 20           moltype = AA  length = 648
FEATURE                 Location/Qualifiers
source                  1..648
                        mol_type = protein
                        organism = synthetic construct
SEQUENCE: 20
METDTLLLWV LLLWVPGSTW EVQLLESGGG LVQPGGSLRL SCAASGFTFS GYYMSWVRQA             60
PGKGLEWVSA ISHSGGSTYY ADSVKGRFTI SRDNSKNTLY LQMNSLRAED TAVYYCAKWG            120
PAFDYWGQGT LVTVSSASTK GPSVFPLAPS SKSTSGGTAA LGCLVKDYFP EPVTVSWNSG            180
ALTSGVHTFP AVLQSSGLYS LSSVVTVPSS SLGTQTYICN VNHKPSNTKV DKKVEPKSCD            240
KTHTCPPCPA PELLGGPSVF LFPPKPKDTL MISRTPEVTC VVVDVSHEDP EVKFNWYVDG            300
VEVHNAKTKP REEQYNSTYR VVSVLTVLHQ DWLNGKEYKC KVSNKALPAP IEKTISKAKG            360
QPREPQVYTL PPSRDELTKN QVSLTCLVKG FYPSDIAVEW ESNGQPENNY KTTPPVLDSD            420
GSFFLYSKLT VDKSRWQQGN VFSCSVMHEA LHNHYTQKSL SLSPGKAEAA AKEAAAKEAA            480
AKASYNLLGF LQRSSNFQCQ KLLWQLNGTL EYCLKDRMNF DIPEEIKQLQ QFQKEDAALT            540
IYEMLQNIFA IFRQDSSSTG WNETIVENLL ANVYHQINHL KTVLEEKLEK EDFTRGKLMS            600
SLHLKRYYGR ILHYLKAKEY SHCAWTIVRV EILRNFYFIN RLTGYLRN                         648

SEQ ID NO: 21           moltype = AA  length = 652
FEATURE                 Location/Qualifiers
```

```
                          -continued source                    1..652
                          mol_type = protein
                          organism = synthetic construct
SEQUENCE: 21
METDTLLLWV LLLWVPGSTG EVQLVESGGG LVQPGGSLRL SCAASGFNIK DTYIHWVRQA    60
PGKGLEWVAR IYPTNGYTRY ADSVKGRFTI SADTSKNTAY LQMNSLRAED TAVYYCSRWG   120
GDGFYAMDYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK AEAAAKEAAA   480
KEAAAKASYN LLGFLQRSSN FQCQKLLWQL NGTLEYCLKD RMNFDIPEEI KQLQQFQKED   540
AALTIYEMLQ NIFAIFRQDS SSTGWNETIV ENLLANVYHQ INHLKTVLEE KLEKEDFTRG   600
KLMSSLHLKR YYGRILHYLK AKEYSHCAWT IVRVEILRNF YFINRLTGYL RN           652

SEQ ID NO: 22             moltype = DNA   length = 21
FEATURE                   Location/Qualifiers
source                    1..21
                          mol_type = other DNA
                          organism = synthetic construct
SEQUENCE: 22
gggtccacaa gaccttcaag t                                              21

SEQ ID NO: 23             moltype = DNA   length = 20
FEATURE                   Location/Qualifiers
source                    1..20
                          mol_type = other DNA
                          organism = synthetic construct
SEQUENCE: 23
tgcagctgag ctaggtacga                                                20

SEQ ID NO: 24             moltype = DNA   length = 20
FEATURE                   Location/Qualifiers
source                    1..20
                          mol_type = other DNA
                          organism = synthetic construct
SEQUENCE: 24
agacccttgt gctcgttgtc                                                20

SEQ ID NO: 25             moltype = DNA   length = 20
FEATURE                   Location/Qualifiers
source                    1..20
                          mol_type = other DNA
                          organism = synthetic construct
SEQUENCE: 25
ttgttgggtg atcagagcag                                                20

SEQ ID NO: 26             moltype = DNA   length = 19
FEATURE                   Location/Qualifiers
source                    1..19
                          mol_type = other DNA
                          organism = synthetic construct
SEQUENCE: 26
cagtccaccc cctgaaaaa                                                 19

SEQ ID NO: 27             moltype = DNA   length = 20
FEATURE                   Location/Qualifiers
source                    1..20
                          mol_type = other DNA
                          organism = synthetic construct
SEQUENCE: 27
ggaccttgag ttggacttgc                                                20

SEQ ID NO: 28             moltype = DNA   length = 20
FEATURE                   Location/Qualifiers
source                    1..20
                          mol_type = other DNA
                          organism = synthetic construct
SEQUENCE: 28
atggccaatt ctgccataag                                                20

SEQ ID NO: 29             moltype = DNA   length = 21
FEATURE                   Location/Qualifiers
source                    1..21
                          mol_type = other DNA
                          organism = synthetic construct
SEQUENCE: 29
tgactgtgca gtccctagct t                                              21
```

```
SEQ ID NO: 30          moltype = DNA  length = 20
FEATURE                Location/Qualifiers
source                 1..20
                       mol_type = other DNA
                       organism = synthetic construct
SEQUENCE: 30
gacaagcctg tagcccatgt                                                     20

SEQ ID NO: 31          moltype = DNA  length = 18
FEATURE                Location/Qualifiers
source                 1..18
                       mol_type = other DNA
                       organism = synthetic construct
SEQUENCE: 31
tctcagctcc acgccatt                                                       18

SEQ ID NO: 32          moltype = DNA  length = 22
FEATURE                Location/Qualifiers
source                 1..22
                       mol_type = other DNA
                       organism = synthetic construct
SEQUENCE: 32
cctcagagag tagcagctca ca                                                  22

SEQ ID NO: 33          moltype = DNA  length = 21
FEATURE                Location/Qualifiers
source                 1..21
                       mol_type = other DNA
                       organism = synthetic construct
SEQUENCE: 33
cagagccttt tcattcttgg a                                                   21
```

METHOD FOR TREATING OR SENSITIZING INTERFERON BETA RESISTANT CANCER COMPRISING CFLIP SIRNA

CROSS-REFERENCE TO RELATED APPLICATIONS

This application is a continuation of U.S. application Ser. No. 16/321,409, filed on Jan. 28, 2019, which is a § 371 national phase of International Application No. PCT/KR2017/008239, filed on Jul. 31, 2017, which claims the benefit of Korean Patent Application No. 10-2016-0097516 filed Jul. 29, 2016, which applications are incorporated by reference herein.

TECHNICAL FIELD

The present invention relates to a composition comprising cFLIP siRNA for the treatment or sensitization of an interferon-beta-resistant cancer disease and, more specifically, to a pharmaceutical composition for treatment of an interferon-beta-resistant cancer disease, the composition comprising, as active ingredients: (a) siRNA which binds to mRNA of cFLIP gene; and (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1, and to a composition comprising cFLIP siRNA as an active ingredient for the sensitization of interferon-beta-resistant cancer cells.

BACKGROUND ART

This application claims priority from Korean Patent Application No. 10-2016-0097516 filed with the Korean Intellectual Property Office (KIPO) on 29 Jul. 2016, the disclosure of which is incorporated herein by reference in its entirety.

Interferons (IFNs), which belong to a class of cytokines, show antiviral activity, inhibit cell proliferation, and regulate natural immune responses. Among interferons, interferon-beta (IFNβ or IFN-β) belonging to Type 1 interferons is a spherical protein of 22 kDa with five alpha-helices, and the size thereof is 18 kDa after the removal of glycans (Arduini et al., *Protein Science,* 8:1867-1877, 1999).

The clinical applications of interferon-beta has been being extensively and actively studied. It has been reported that interferon-beta is effective in the treatment of multiple sclerosis, cancer, auto-immune disorders, viral infections, HIV-related diseases, hepatitis C, rheumatoid arthritis, and the like, through a variety of immunological activities, such as antiviral activity, cell growth inhibitory or anti-growth activity, lymphocytotoxicity-increasing activity, immuno-regulatory activity, target cell differentiation-inducing or -inhibitory activity, macrophage-activating activity, cytokine production-increasing activity, cytotoxic T cell effect-increasing activity, and natural killer cell-increasing activity (Pilling et al., *European Journal of Immunology,* 29:1041-1050, 1999; Young et al., *Neurology* 51:682-689, 1998; Cirelli et al, *Clin Immunother* 3:27-87, 1995).

In particular, the US Food and Drug Administration approved Type 1 interferons as medicines for various types of carcinoma, such as chronic myelogenous leukemia, melanoma, and renal cell carcinoma in 1988, but the use thereof as anticancer drugs has been recently decreased due to the development of adverse side effects, non-responsiveness, tolerance, and the like. Until recently, interferon-beta has been proved to have anticancer effects through a number of studies, and has been verified to show excellent anticancer efficacy compared with interferon-alpha. However, interferon-beta has not yet been approved as an anticancer drug. Therefore, in order to overcome the side effects of existing interferon-beta and, more importantly, to maximize the anticancer effects of interferon-beta, the development of sensitizers that can increase the sensitivity of interferon-resistant cancer to chemotherapy is urgent.

DETAILED DESCRIPTION OF THE INVENTION

Technical Problem

Therefore, the present inventors confirmed that the inhibition of the expression levels of cFLIP in cancer cells can sensitize cancer cells and improve anticancer effects of interferon-beta, and thus completed the present invention.

An aspect of the present invention is to provide a pharmaceutical composition for the treatment of an interferon-beta-resistant cancer disease, the composition comprising, as active ingredients:
(a) siRNA which binds to mRNA of cFLIP gene in a complementary manner; and
(b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

Another aspect of the present invention is to provide use of (a) siRNA and (b) a human interferon-beta mutant for preparing an agent for the treatment of an interferon-beta-resistant cancer disease,
wherein the siRNA (a) binds to mRNA of cFLIP gene in a complementary manner, and
wherein the human interferon-beta mutant (b) comprises a glycine-asparagine-isoleucine-threonine-valine (GNITV) sequence at the C-terminus, or threonine or serine is substituted for arginine at the 27th amino acid, in a wild-type human interferon-beta amino acid sequence defined by SEQ ID NO: 1.

Another aspect of the present invention is to provide a method for treating an interferon-beta-resistant cancer disease, the method comprising administering an effective amount of a composition to a subject in need thereof,
wherein the composition comprises, as active ingredients: (a) siRNA which binds to mRNA of cFLIP gene in a complementary manner; and (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1.

Another aspect of the present invention is to provide a composition for sensitizing interferon-beta-resistant cancer cells, the composition comprising, as an active ingredient, siRNA which binds to mRNA of cFLIP gene in a complementary manner.

Still another aspect of the present invention is to provide use of siRNA for preparing an agent for sensitizing interferon-beta-resistant cancer cells, wherein the siRNA binds to mRNA of cFLIP gene in a complementary manner.

Still another aspect of the present invention is to provide a method for sensitizing interferon-beta-resistant cancer cells, the method comprising administering an effective amount of a composition to a subject in need thereof, wherein the composition comprises, as an active ingredient, siRNA which binds to mRNA of cFLIP gene in a complementary manner.

Technical Solution

In accordance with an aspect of the present invention, there is provided a pharmaceutical composition for the treatment of an interferon-beta-resistant cancer disease, the composition comprising, as active ingredients:
(a) siRNA which binds to mRNA of cFLIP gene in a complementary manner; and
(b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

Further, there is provided a pharmaceutical composition for the treatment of an interferon-beta-resistant cancer disease, the composition consisting of:
(a) siRNA which binds to mRNA of cFLIP gene in a complementary manner; and
(b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

Furthermore, there is provided a pharmaceutical composition for the treatment of an interferon-beta-resistant cancer disease, the composition consisting essentially of:
(a) siRNA which binds to mRNA of cFLIP gene in a complementary manner; and
(b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

In accordance with another aspect of the present invention, there is provided use of (a) siRNA and (b) a human interferon-beta mutant for preparing an agent for the treatment of an interferon-beta-resistant cancer disease,
wherein the siRNA (a) binds to mRNA of cFLIP gene in a complementary manner, and
wherein the human interferon-beta mutant (b) comprises a glycine-asparagine-isoleucine-threonine-valine (GNITV) sequence at the C-terminus, or threonine or serine is substituted for arginine at the 27th amino acid, in a wild-type human interferon-beta amino acid sequence defined by SEQ ID NO: 1.

In accordance with another aspect of the present invention, there is provided a method for treating an interferon-beta-resistant cancer disease, the method comprising administering an effective amount of a composition to a subject in need thereof,
wherein the composition comprises, as active ingredients:
(a) siRNA which binds to mRNA of cFLIP gene in a complementary manner; and (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1.

Further, there is provided a method for treating an interferon-beta-resistant cancer disease, the method comprising administering an effective amount of a composition to a subject in need thereof,
wherein the composition consists of: (a) siRNA which binds to mRNA of cFLIP gene in a complementary manner; and (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1.

Furthermore, there is provided a method for treating an interferon-beta-resistant cancer disease, the method comprising administering an effective amount of a composition to a subject in need thereof,
wherein the composition consists essentially of: (a) siRNA which binds to mRNA of cFLIP gene in a complementary manner; and (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1.

In accordance with another aspect of the present invention, there is provided a composition for sensitizing interferon-beta-resistant cancer cells, wherein the composition comprises, as an active ingredient, siRNA which binds to mRNA of cFLIP gene in a complementary manner.

Further, there is provided a composition for sensitizing interferon-beta-resistant cancer cells, wherein the composition consists of siRNA which binds to mRNA of cFLIP gene in a complementary manner.

Furthermore, there is provided a composition for sensitizing interferon-beta-resistant cancer cells, wherein the composition consists essentially of siRNA which binds to mRNA of cFLIP gene in a complementary manner.

In accordance with still another aspect of the present invention, there is provided use of siRNA for preparing an agent for sensitizing interferon-beta-resistant cancer cells, wherein the siRNA binds to mRNA of cFLIP gene in a complementary manner.

In accordance with still another aspect of the present invention, there is provided a method for sensitizing interferon-beta-resistant cancer cells, the method comprising administering an effective amount of a composition to a subject in need thereof, wherein the composition comprises, as an active ingredient, siRNA which binds to mRNA of cFLIP gene in a complementary manner.

Further, there is provided a method for sensitizing interferon-beta-resistant cancer cells, the method comprising administering an effective amount of a composition to a subject in need thereof, wherein the composition consists of siRNA which binds to mRNA of cFLIP gene in a complementary manner.

Furthermore, there is provided a method for sensitizing interferon-beta-resistant cancer cells, the method comprising administering an effective amount of a composition to a subject in need thereof, wherein the composition consists essentially of siRNA which binds to mRNA of cFLIP gene in a complementary manner.

Hereinafter, the present invention will be described in detail.

The present invention provides a pharmaceutical composition for the treatment of an interferon-beta-resistant cancer disease, the composition comprising, as active ingredients:
(a) siRNA which binds to mRNA of cFLIP gene in a complementary manner; and
(b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

The present inventors found that, as a result of comparing expression patterns of proteins associated with cell apoptosis and death receptor signaling after cancer cells, of which apoptosis occurs in response to interferon-beta (IFNβ or IFN-β), and IFNβ-resistant cancer cells were treated with Carbiferon as an IFNβ mutant, the expression rate of cFLIP was increased by IFNβ treatment in the IFNβ-resistant cancer cells. Furthermore, the present inventors confirmed that when the expression of cFLIP was inhibited using siRNA in IFNβ-resistant cancer cells, caspase-8 and the like, which are important for cell apoptosis, were activated in the IFNβ-resistant cancer cells in response to Carbiferon, thereby greatly reducing cell viability, so that the cancer cell apoptotic effect of Carbiferon was exerted. Therefore, the present invention provides a composition comprising cFLIP siRNA as an active ingredient for sensitization, the composition allowing IFNβ-resistant cancer cells to induce cell apoptosis thereof in response to IFNβ. Furthermore, the present invention provides a pharmaceutical composition effective in treating an IFNβ-resistant cancer disease by the co-administration of IFNβ or a mutant thereof and cFLIP siRNA.

As used herein, "polynucleotide" or "nucleic acid" refers to a single-stranded or double-stranded deoxyribonucleic acid (DNA) or ribonucleic acid (RNA). Unless otherwise limited, the polynucleotide or nucleic acid includes known analogs of natural nucleotides that hybridize with nucleic acids in a manner similar to naturally occurring nucleotides. In general, DNA is composed of four types of bases including adenine (A), guanine (G), cytosine (C), and thymine (T), while RNA has uracil (U) instead of thymine (T). In the double-stranded nucleic acid, base A forms a hydrogen bonding with base T or U, while base C forms a hydrogen bonding with base G. Such a relationship between the bases is referred to as being "complementary".

Here, "messenger RNA (mRNA)" acts as a blueprint RNA for polypeptide synthesis (protein translation) by transferring genetic information of the nucleotide sequence of a particular gene to ribosomes during protein synthesis. Single-stranded mRNA is synthesized through a transcription process using the gene as a template.

As used herein, "protein" is used interchangeably with "polypeptide" or "peptide", and refers to, for example, a polymer of amino acid residues, as typically found in proteins in nature.

As used herein, the single-letter (triple-letter) codes of amino acids refer to the following amino acids according to standard abbreviations in the biochemistry: A (Ala): alanine; C (Cys): cysteine; D (Asp): aspartic acid; E (Glu): glutamic acid; F (Phe): phenylalanine; G (Gly): glycine; H (His): histidine; I (Ile): isoleucine; K (Lys): lysine; L (Leu): leucine; M (Met): methionine; N (Asn): asparagine; O (Ply) pyrrolic acid; P (Pro): proline; Q (Gln): Glutamine; R (Arg): arginine; S (Ser): serine; T (Thr): threonine; U (Sec): selenocysteine, V (Val): valine; W (Trp): tryptophan; Y (Tyr): Tyrosine.

As indicated herein, (amino acid single-letter code) (amino acid position) (amino acid single-letter code) refers to a substitution of the preceding amino acid with the following amino acid at the corresponding amino acid position in a wild-type protein (herein, wild-type human interferon-beta protein defined by SEQ ID NO: 1). For example, R27T means a replacement of arginine, corresponding to the 27th amino acid residue in a normal type protein, with threonine.

As used herein, "expression" refers to the production of a protein or a nucleic acid in cells.

The "cellular FLICE-like inhibitory protein (cFLIP)" is a gene also known as CASH, FLIP, MRIT, CLARP, FLAME, Casper, FLAME1, FLAME-1, I-FLICE, CASP8AP1, or the like, and the official name thereof is "CASP8 and FADD like apoptosis regulator (CFLAR)". cFLIP is structurally similar to caspase-8, but has no proteolytic activity, and regulates cell apoptosis by typical death receptors and pattern recognition receptors.

As used herein, cFLIP gene is derived from humans, and located on chromosome 2q33-34. The human cFLIP gene has transcript variants encoding various isoform proteins, while three representative isoforms thereof are $cFLIP_L$, $cFLIP_R$, and $cFLIP_S$. As used herein, cFLIP preferably refers to $cFLIP_L$ or $cFLIP_S$. $cFLIP_L$ is an approximately 55 kDa protein having two death effector domains (DEDs) at the N-terminus and a caspase-like domain at the C-terminus, while $cFLIP_S$ is an approximately 27 kDa protein having two DEDs without a caspase-like domain.

More specifically, mRNA of the cFLIP gene according to the present invention encodes $cFLIP_L$ or $cFLIP_S$, and may comprise, but is not limited thereto, any one nucleotide sequence selected from the group consisting of SEQ ID NO: 7 and SEQ ID NO: 8.

The "siRNA (small interfering RNA, short interfering RNA, or silencing RNA)" is a short double-stranded RNA, which is artificially introduced into cells to induce the degradation of mRNA of a specific gene, thereby preventing protein translation and leading to RNA interference that inhibits gene expression. The siRNA is composed of 20-25 nucleotides complementary to a particular site of a target mRNA. In cells, a strand complementary to target mRNA (antisense strand), among the double strands of siRNA, binds to target mRNA by binding to an RNA-induced silencing complex (RISC) protein complex, and the argonaute protein in the RISC complex degrades the target mRNA by cleavage, or prevents proteins and ribosomes, which are important in protein translation, from binding to mRNA, thereby inhibiting the expression of a particular gene.

Therefore, cFLIP siRNA, which is an active ingredient of the pharmaceutical composition of the present invention, means a 20- to 25-bp short RNA, which binds to a particular nucleotide sequence on mRNA of cFLIP gene in a complementary manner to resultantly degrade cFLIP mRNA, thereby lowering the expression level of cFLIP gene. The cFLIP siRNA may be any one selected from the group consisting of, specifically, SEQ ID NO: 9 to SEQ ID NO: 13, and most preferably SEQ ID NO: 11 or SEQ ID NO: 12. A target site of cFLIP siRNA on cFLIP mRNA according to the present invention is shown in FIG. 5. In the pharmaceutical composition of the present invention, cFLIP siRNA activates cell apoptosis or death receptor-related signaling pathways in interferon-beta-resistant cancer cells, and thus acts as a sensitizer capable of sensitively responding to an anticancer action of an anticancer drug, most preferably, interferon-beta or a mutant thereof.

The siRNA according to the present invention may be obtained by applying, to oligonucleotides, various modifications for improving in vivo stability of oligonucleotides, providing resistance to nuclease, and reducing non-specific immune responses. The modifications of the oligonucleotides may be a combination of one or more selected from: a modification by a substitution of an OH group with —CH$_3$ (methyl), —OCH$_3$ (methoxy), —NH$_2$, —F, —O-2-methoxyethyl, —O-propyl, —O-2-methylthioethyl, —O-3-aminopropyl, —O-3-dimethylaminopropyl, —O—N-methylacetamido or —O-dimethylamidooxyethyl at the 2' carbon position on the sugar structure in at least one nucleotide; a modification by a substitution of oxygen with sulfur in the sugar structure in the nucleotide; or a modification by a substitution of a nucleotide bond with a phosphorothioate bond, a boranophosphate bond, or methyl phosphonate bond. A modification into a form of peptide nucleic acid (PNA), locked nucleic acid (LNA), or unlocked nucleic acid (UNA) may also be used.

Another active ingredient of the pharmaceutical composition of the present invention is a human interferon-beta mutant having anticancer activity, wherein the mutant comprises a glycine-asparagine-isoleucine-threonine-valine sequence (GNITV) at the C-terminus, or threonine (R27T) or serine (R27S) is substituted for arginine at the 27th amino acid, in a wild-type human interferon-beta amino acid sequence defined by SEQ ID NO: 1. The human interferon-beta mutant is obtained by adding at least one N-linked glycan to the wild-type human interferon-beta, wherein The GNITV sequence is added at the C-terminus of the wild-type interferon-beta polypeptide (SEQ ID NO: 1) so that N-linked glycosylation occurs in asparagine at the position thereof, or through the introduction of an amino acid substitution, R27T or R27S, into the wild-type interferon-beta polypeptide (SEQ ID NO: 1), the amino acid sequence of a corresponding site, that is, the sequence of the 25th to 28$^{th}$ amino acids is changed into asparagine-glycine-threonine/serine-leucine (NG(T/S)L) to induce N-linked glycosylation at the position thereof.

The interferon mutant, compared with its wild type, has improved antiviral activity, cell growth inhibitory activity, immunoregulatory functions, in vivo half-life and stability, which is disclosed in more detail in Korean Patent No. 10-0781666 and PCT Application No. PCT/KR2016/002129.

Specifically, the human interferon-beta mutant may include any one amino acid sequence selected from the group consisting of SEQ ID NO: 2 to SEQ ID NO: 6.

The interferon-beta mutant of the present invention also includes a functional equivalent of a polypeptide comprising an amino acid sequence defined by any one of SEQ ID NO: 2 to SEQ ID NO: 6. The "functional equivalent" refers to a polypeptide having at least 70%, preferably at least 80%, and more preferably at least 90% sequence homology (that is, identity) to the amino acid sequence defined by the above mentioned sequence number. For example, the functional equivalent encompasses polypeptides having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% sequence homology, and refers to a polypeptide exhibiting substantially identical physiological activity to the polypeptide defined by the above mentioned sequence number. Here, the "substantially identical physiological activity" refers to having equivalent or superior activity to a wild-type (WT) human interferon-beta by retaining the same N-linked glycosylation as the polypeptide comprising an amino acid sequence defined by any one of SEQ ID NO: 2 to SEQ ID NO: 6.

Various examples of such activity of the human interferon-beta may include multiple sclerosis-alleviating, -ameliorating, or -treating activity, antiviral activity, cell growth inhibitory activity, anti-growth activity, anti-proliferative activity, lymphocytotoxicity-increasing activity, immunoregulatory activity, target cell differentiation-inducing or -inhibitory activity, cytokine production-increasing activity, cytotoxic T cell effect-increasing activity, macrophage effect-increasing activity, natural killing cell-increasing activity, cancer-preventing or -treating activity, auto-immune disorder-preventing or -treating activity, viral infection-preventing or -treating activity, HIV-related disease-preventing or -treating activity, hepatitis C-preventing or -treating activity, rheumatoid arthritis-preventing or -treating activity, and the like. For the purposes of the present invention, the "activity of human interferon-beta" refers to an anti-cancer activity which inhibits cancer cell proliferation and induces cell apoptosis.

Interferon-beta has an anticancer activity by inhibiting the proliferation of cancer cells and inducing cell apoptosis through various mechanisms. Interferon-beta inhibits the growth of tumor cells by inhibiting tumor cell angiogenesis, or induces tumor cell apoptosis by inducing innate or acquired immune responses in environments around tumor sites, thereby exhibiting anticancer effects. Furthermore, interferon-beta acts directly on cancer cells to regulate main cell apoptosis-related signaling, such as extrinsic death receptor pathways and intrinsic mitochondrial pathways, responding to extracellular stimuli (Parker B et al., *Nat. Rev. Cancer.*, 16:131-144, 2016).

The functional equivalent may be produced as a result of an addition, a substitution, or a deletion of a portion of an amino acid sequence defined by any one of SEQ ID NO: 2 to SEQ ID NO: 6. In the above, the substitution of amino acid is preferably a conservative substitution. Examples of the conservative substitution of a naturally occurring amino acid are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). The functional equivalent also encompasses mutants in which some amino acids are deleted on the amino acid sequence of the interferon-beta mutant polypeptide of the present invention. The deletion or substitution of amino acid is preferably located at a region that is not directly associated with physiological activity of the polypeptide of the present invention. Also, the deletion of amino acid is preferably located at a region that is not directly involved in physiological activity of the polypeptide of the amino acid sequence defined by the above mentioned sequence number. The functional equivalent also includes variants in which some amino acids are added to both termini of the amino acid sequence of the polypeptide or within the amino acid sequence thereof. Also, the functional equivalent of the present invention also covers polypeptide derivatives that have some modifications to the chemical structure of the polypeptide according to the present invention while maintaining the fundamental backbone and physiological activity thereof. For example, the functional equivalent of the present invention also includes a structural modification for changing stability, storability, volatility, or solubility of the polypeptide of the present invention.

Furthermore, the human interferon-beta mutant according to the present invention may be a fusion protein in which an antibody or an antibody fragment thereof is bound. Since interferon-beta is expressed in various tissues and cells, the interferon-beta mutant, in which a protein or a polymeric substance expressed specifically in cancer cells so as to allow anti-proliferative activity and cell apoptotic activity of the interferon-beta to be focused on cancer cells, that is, an antibody specifically recognizing a tumor antigen is bound, can be expected to lower side effects and have better therapeutic effects as a cancer-targeting drug. Specifically, the human interferon-beta mutant according to the present invention may comprise any one amino acid sequence selected from the group consisting of SEQ ID NO: 18 to SEQ ID NO: 21.

The tumor antigen is a protein that is produced by tumor cells that elicits an immune response, especially, a T cell-mediated immune response. Tumor antigens are well known in the art, and examples thereof include a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2(AS), intestinal carboxyl esterase, mut hsp70-2, M-CSF, prostase, prostate-specific antigen (PSA), PAP, NY-ESO-1, LAGE-Iα, p53, prostein, PSMA, Her2/neu, survivin and telomerase, prostate-carcinoma tumor antigen-1 (PCTA-1), MAGE, ELF2M, neutrophil elastase, ephrin-B2, CD22, insulin growth factor (IGF)-I, IGF-II, IGF-I receptor, or mesothelin.

The type of tumor antigen designated herein may also be a tumor-specific antigen (TSA) or a tumor-associated antigen (TAA). TSA is unique to tumor cells, and is not produced in the other cells of the body. TAA-associated antigen is not unique to tumor cells and, instead, is expressed in normal cells under conditions in which a state of immunologic tolerance to an antigen is not induced. The expression of antigens to tumors may occur under conditions in which immune systems are allowed to respond to the antigens. TAA may be an antigen that is expressed in normal cells during fetal development when immune systems are immature and unable to respond, or may be an antigen that is normally present at an extremely low level in normal cells but expressed at a significantly high level in tumor cells.

Non-limiting examples of TSA or TAA include:
differentiation antigens, such as MART-l/MelanA (MART-I), gp100 (Pmel 17), tyrosinase, TRP-1, and TRP-2, and tumor-specific multi-lineage antigens, such as MAGE-1, MAGE-3, BAGE, GAGE-1, GAGE-2, and p15; overexpressed embryonic antigens, such as CEA; overexpressed oncogenes, and mutated tumor-suppressor genes, such as p53, Ras, and HER-2/neu; unique tumor antigens resulting from chromosomal translocations, such as BCR-ABL, E2A-PRL, H4-RET, IGH-IGK, MYL-RAR; and viral antigens, such as Epstein Barr virus antigen EBVA and human papillomavirus (HPV) antigen E6 and E7. Other large, protein-based antigens include: TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-related protein, TAAL6, TAG72, TLP, and TPS.

Examples of antibodies specifically recognizing the tumor antigens may include, but are not limited to, HuM195 (e.g., Kossman et al., *Clin. Cancer Res.*, 5:2748-2755, 1999), CMA-676 (e.g., Sievers et al., *Blood*, 93:3678-3684, 1999), AT13/5 (e.g., Ellis et al., *J. Immunol.* 155:925-937, 1995), HB7, trastuzumab (e.g., Herceptin; Fornier et al., *Oncology (Huntingt)*, 13:647-58, 1999), TAB-250 (Rosenblum et al., *Clin. Cancer Res.*, 5:865-874, 1999), BACH-250, TA1 (Maier et al., *Cancer Res.*, 51:5361-5369, 1991) and U.S. Pat. No. 5,772,997; mAb (mAb 4D5; ATCC CRL10463) described in U.S. Pat. No. 5,770,195; and mAb described in U.S. Pat. No. 5,677,171, Mc5 (e.g., Peterson et al., *Cancer Res.*, 57:1103-1108, 1997; Ozzello et al., *Breast Cancer Res. Treat.*, 25:265-276, 1993), hCTMO1 (e.g., Van Y M et al., *Cancer Res.*, 56:5179-5185, 1996), CC49 (e.g., Pavlinkova et al., *Clin. Cancer Res.*, 5:2613-2619, 1999), B72.3 (e.g., Divgi et al., *Nucl. Med. Biol.*, 21:9-15, 1994), mouse clonal anti-HM1.24 IgG2a/κ, humanized anti-HM1.24 IgG1/κ antibody (e.g., Ono et al., *Mol. Immuno.*, 36:387-395, 1999), rituximab, ibritumomabtiuxetan and tositumomab, AME-133v (Applied Molecular Evolution), ocrelizumab (Roche), ofatumumab (Genmab), TRU-015 (Trubion), IMMU-106 (Immunomedics), and the like.

The antibody of the present invention may be a human antibody, a chimeric antibody, and/or a humanized antibody, but is not limited thereto. The chimeric antibody means an antibody composed of a variable region of murine immunoglobulin and a constant region of human immunoglobulin. Such alternation is simply configured of a substitution of a human antibody constant region with a murine constant region, and thus producing a human/murine chimera capable of having sufficiently low immunogenicity so as to allow pharmaceutical use.

The "humanized antibody" means an antibody (wholly or partially) composed of an amino acid sequence derived from the human antibody germline by modifying the sequence of an antibody having a non-human complementarity-determining region (CDR). The humanization of antibody variable region and CDR is carried out by a technique well known in the art. Such an antibody is needed for Fc-dependent effector function, but retains a human constant region, which is significantly less likely to induce an immune response to the antibody. As an example, the framework regions of the variable regions are substituted by corresponding human framework regions leaving the non-human CDR substantially intact, or even replacing CDR with sequences derived from the human genome (See e.g., Patent application US 2006/25885). Fully human antibodies are produced in genetically modified mice, of which immune systems have been altered to correspond to human immune systems. A humanized antibody also refers to an antibody encompassing a human framework, at least one CDR from a non-human antibody, in which any constant region present is substantially identical to a human immunoglobulin constant region, i.e., at least about 85% or 90%, and preferably at least 95% identical. Hence, all parts of a humanized antibody (probably except for CDRs) are substantially identical to corresponding parts of at least one natural human immunoglobulin sequence.

As used herein, the "antibody fragment" refers to an antibody fragment capable of responding to the same antigen as an antibody counterpart thereof. Such fragments can be simply identified by a person skilled in the art, and may include, for example, $F_{ab}$ fragment (e.g., a fragment by papain digestion), $F_{ab}'$ fragment (e.g., a fragment by pepsin digestion and partial reduction), $F_{(ab')_2}$ fragment (e.g., a fragment by pepsin digestion), $F_{acb}$ fragment (e.g., a fragment by plasmin digestion), $F_d$ fragment (e.g., a fragment by pepsin digestion, partial reduction, and reaggregation), and $scF_v$ fragment (single chain Fv; e.g., a fragment by molecular biology techniques) fragment. Such fragments can be produced by enzymatic cleavage, synthetic, or recombinant techniques, as known in the art and/or as described herein.

As used herein, the term "treatment" or "treating" refers to suppressing the occurrence or recurrence of diseases, alleviating symptoms, reducing direct or indirect pathological consequences of disease, reducing disease progression rates, improving, bettering, or relieving disease conditions, or improving prognosis. The disease to be treated in the present invention is an interferon-beta-resistant cancer disease.

The pharmaceutical composition for treatment of an interferon-beta-resistant cancer disease is not limited to the type of cancer disease as long as the type of cancer does not respond to an anticancer action of interferon. Examples of the interferon-beta-resistant cancer disease may be any one selected from the group consisting of breast cancer, gastric cancer, ovarian cancer, lung cancer, colon cancer, anal cancer, astrocytoma, leukemia, lymphoma, head and neck cancer, liver cancer, testicular cancer, cervical cancer, sarcoma, hemangioma, esophageal cancer, eye cancer, laryngeal cancer, oral cancer, mesothelioma, myeloma, oral cavity cancer, rectal cancer, throat cancer, bladder cancer, uterine cancer, prostate cancer, large intestine cancer, pancreatic cancer, renal cancer, skin cancer, basal cell carcinoma, melanoma, squamous cell carcinoma, oral squamous cell carcinoma, colorectal cancer, glioblastoma, endometrial cancer, and malignant glioma.

The pharmaceutical composition according to the present invention may be variously formulated together with a pharmaceutically acceptable carrier, depending on the route of administration, for anticancer action or cancer cell sensitization. The carrier includes all kinds of solvents, dispersion media, oil-in-water or water-in-oil emulsions, aqueous compositions, liposomes, microbeads, and microsomes.

The pharmaceutical composition according to the present invention may be administered to a patient in a pharmaceutically effective amount, that is, an amount sufficient to sensitize interferon-beta-resistant cancer and to exhibit an anticancer effect when administered in combination with human interferon-beta or a mutant thereof. For example, a general daily dose may be in the range of about 0.01-1000 mg/kg, and preferably in the range of about 1-100 mg/kg. The pharmaceutical composition of the present invention may be administered once or several times in a divided dose within a preferable dose range. The dose of the pharmaceutical composition according to the present invention may be appropriately determined by a person skilled in the art depending on the route of administration, subject to be administered, age, gender, weight, individual difference, and disease state.

The route of administration may be an oral or parenteral route. The parenteral administration method includes, but is not limited to, intravenous, intramuscular, intraarterial, intramedullary, intradermal, intracardiac, transdermal, subcutaneous, intraperitoneal, intranasal, intestinal enteric, topical, sublingual, or rectal administration.

The pharmaceutical composition of the present invention, when orally administered, may be formulated, together with a suitable carrier for oral administration, in the form of powders, granules, tablets, pills, sugar-coated tablets, capsules, liquid, gel, syrup, suspension, wafer, or the like, by a method known in the art. Examples of the suitable carrier may include: saccharides including lactose, dextrose, sucrose, sorbitol, mannitol, xylitol, erythritol, and maltitol; starches including corn starch, wheat starch, rice starch, and potato starch; celluloses including cellulose, methyl cellulose, sodium carboxy methyl cellulose, and hydroxypropyl methyl cellulose; and fillers, such as gelatin and polyvinyl pyrrolidone. In some cases, cross-linked polyvinyl pyrrolidone, agar, alginic acid, sodium alginate, or the like may be added as a disintegrant. Furthermore, the pharmaceutical composition may further comprises an anti-coagulant, a lubricant, a wetting agent, a fragrance, an emulsifier, a preservative, and the like.

As for the parenteral administration, the pharmaceutical composition of the present invention may be formulated in a dosage form of an injection, a transdermal administration preparation, and a nasal inhalant, together with a suitable parenteral carrier, by a method known in the art. The injection needs to be essentially sterilized, and needs to be protected from the contamination of microorganisms, such as bacteria and fungus. Examples of the suitable carrier for the injection may be a solvent or a dispersion medium containing water, ethanol, a polyol (e.g., glycerol, propylene glycol, liquid polyethylene glycol, etc.), a mixture thereof, and/or vegetable oil, but are not limited thereto. More preferably, the suitable carrier may be an isotonic solution, such as Hank's solution, Ringer's solution, phosphate buffered saline (PBS) containing triethanol amine) or sterilized water for injection, 10% ethanol, 40% propylene glycol, and 5% dextrose. In order to protect the injection against microbial contamination, the injection may further contain various antimicrobial and antifungal agents, such as paraben, chlorobutanol, phenol, sorbic acid, and thimerosal. In most cases, the injection may further contain sugar or an isotonic agent, such as sodium chloride.

The dosage form of the transdermal administration preparation includes an ointment, a cream, a lotion, a gel, a solution for external application, a paste, a liniment, and an aerosol. The "transdermal administration" means the delivery of an effective amount of an active ingredient contained in the pharmaceutical composition into the skin by the local administration of the pharmaceutical composition into the skin. For example, the pharmaceutical composition of the present invention may be prepared into an injection formulation, which is then administered by slight pricking of the skin using a 30-gauge needle or direct application to the skin. These formulations are described in the literature, which is a formulary generally known in pharmaceutical chemistry (Remington's Pharmaceutical Science, 15th Edition, 1975, Mack Publishing Company, Easton, Pa.).

As for an inhalational administration preparation, the compound used according to the present invention may be conveniently delivered in the form of an aerosol spray from a pressurized pack or a nebulizer by using a suitable propellant, such as dichlorofluoromethane, trichlorofluoromethane, dichlorotetrafluoroethane, or carbon dioxide, or another suitable gas. As for a pressurized aerosol, the dose may be determined by providing a valve that delivers a metered amount. For example, a gelatin capsule and a cartridge used in an inhaler or an insufflator may be formulated to contain a powder mixture of a compound and a suitable powder base material, such as lactose or starch.

Other pharmaceutically acceptable carriers are referenced in the following literature (Remington's Pharmaceutical Sciences, 19th ed., Mack Publishing Company, Easton, Pa., 1995).

The pharmaceutical composition according to the present invention may further contain at least one buffer (e. g., saline solution or PBS), carbohydrate (e. g., glucose, mannose, sucrose, or dextran), antioxidant, bacteriostat, chelating agent (e. g., EDTA or glutathione), adjuvant (e. g., aluminum hydroxide), suspending agent, thickener, and/or preservative.

The pharmaceutical composition of the present invention may also be formulated by a method known in the art so as to provide rapid, continuous, or delayed release of an active ingredient after administration to a mammal.

In addition, the pharmaceutical composition of the present invention may be administered alone or in combination with a known compound having an anticancer effect or an effect of sensitizing interferon-beta-resistant cancer.

In addition, the present invention provides a composition for sensitizing interferon-beta-resistant cancer cells, the composition comprising, as an active ingredient, siRNA which binds to mRNA of cFLIP gene in a complementary manner.

The "composition for sensitizing interferon-beta-resistant cancer cells" refers to a composition that increases the sensitivity to cell apoptosis of cancer cells not responding to the stimulation of the interferon-beta, thereby allowing the interferon-beta or a mutant thereof to exhibit anticancer therapeutic effects thereof. The mechanisms by which siRNA, inhibiting the expression of cFLIP gene found by the present inventors, sensitizes interferon-beta-resistant cancer cells are as described above.

The siRNA which binds to mRNA of cFLIP gene in a complementary manner is for preventing the expression of all the various isoforms of cFLIP by effectively inhibiting the expression of the human cFLIP gene. Specifically, the siRNA may comprise any one nucleotide sequence selected from the group consisting of SEQ ID NO: 9 to SEQ ID NO: 13.

In addition, the composition for sensitization according to the present invention may be administered with an anticancer drug simultaneously or sequentially. That is, the composition for sensitization according to the present invention may be administered separately before or after the anticancer drug with a time interval therebetween. The method of administration and route of administration are as described with respect to the pharmaceutical composition of the present invention.

For the purposes of the present invention, the anticancer drug means human interferon-beta or a mutant thereof, and preferably an interferon-beta mutant comprising any one amino acid sequence selected from the group consisting of SEQ ID NO: 2 to SEQ ID NO: 6. In addition, the human interferon-beta mutant may be a protein in a form in which an antibody binding a cancer-specific marker or a fragment thereof is fused or bound, so that the human interferon-beta mutant can selectively focus on cancer cell tissues in the body. Specifically, the interferon-beta mutant in a form in which an antibody or a fragment thereof is fused or bound may comprise any one amino acid sequence selected from the group consisting of SEQ ID NO: 18 to SEQ ID NO: 21.

The composition for sensitization according to the present invention is prepared into a formulation that is optimized for sensitizing interferon-resistant cancer cells, which may be the same formulation as the human interferon-beta mutant, or may be prepared into different formulation in accordance with circumstances.

The type of cancer disease, to which the composition for sensitization of the present invention can be applied, is not limited as long as the cancer disease is an interferon-beta-resistant cancer disease. Specific types of the cancer disease are as described with respect to the pharmaceutical composition of the present invention.

In addition, the present invention provides use of (a) siRNA and (b) a human interferon-beta mutant for preparing an agent for the treatment of an interferon-beta-resistant cancer disease, wherein the siRNA (a) binds to mRNA of cFLIP gene in a complementary manner; and wherein the human interferon-beta mutant (b) comprises a glycine-asparagine-isoleucine-threonine-valine (GNITV) sequence at the C-terminus, or threonine or serine is substituted for arginine at the 27th amino acid, in a wild-type human interferon-beta amino acid sequence defined by SEQ ID NO: 1.

In addition, the present invention provides a method for the treatment of an interferon-beta-resistant cancer disease, the method comprising administering an effective amount of a composition to a subject in need thereof, the composition comprising, as active ingredients, (a) siRNA which binds to mRNA of cFLIP gene in a complementary manner; and (b) a human interferon-beta mutant which comprises a glycine-asparagine-isoleucine-threonine-valine (GNITV) sequence at the C-terminus, or in which threonine or serine is substituted for arginine at the 27th amino acid, in a wild-type human interferon-beta amino acid sequence defined by SEQ ID NO: 1.

In addition, the present invention provides use of siRNA for preparing an agent for sensitizing interferon-beta-resistant cancer cells, wherein the siRNA binds to mRNA of cFLIP gene in a complementary manner.

In addition, the present invention provides a method for sensitizing interferon-beta-resistant cancer cells, the method comprising administering an effective amount of a composition to a subject in need thereof, wherein the composition comprises, as an active ingredient, siRNA which binds to mRNA of cFLIP gene in a complementary manner.

As used herein, the "effective amount" refers to an amount showing effects of treating an interferon-beta-resistant cancer disease or sensitizing interferon-beta-resistant cancer cells when the composition is administered to a subject. The "subject" may be an animal, preferably a mammal, especially an animal including a human being, and may be cells, tissues, and organs, or the like originated from an animal. The subject may be a patient requiring the effects.

As used herein, the "agent or composition" may be a form of a food composition, a cosmetic composition, a pharmaceutical composition and the like, and may mean preferably a pharmaceutical composition in the present invention, which is as described above.

As used herein, the term "comprising" is used synonymously with "containing" or "being characterized", and does not exclude additional ingredients or steps not mentioned in the composition or method. The term "consisting of" means excluding additional elements, steps, or ingredients not otherwise specified. The term "consisting essentially of" means including the mentioned elements or steps as well as any element or step that does not substantially affect basic characteristics thereof in the scope of compositions or methods.

Advantageous Effects

Accordingly, the present invention provides a pharmaceutical composition for treating an interferon-beta-resistant cancer disease, the composition comprising, as active ingredients, siRNA which binds to mRNA of cFLIP gene in a complementary manner and an interferon-beta mutant; and a composition for sensitizing interferon-beta-resistant cancer cells, the composition comprising cFLIP siRNA as an active ingredient. The compositions of the present invention have an effect of promoting cell apoptosis of cancer cells by lowering the expression level of cFLIP in cancer cells showing resistance or tolerance to interferon-beta to not respond to the interferon-beta.

BRIEF DESCRIPTION OF THE DRAWINGS

FIG. 1A shows cell viability (bar graph; upper panel) and microscopic cell images (lower panel) according to the concentration and treatment time of Carbiferon. FIG. 1B shows qPCR results confirming the effects of Carbiferon (100 ng/ml) on the expression levels of death receptor-related genes. FIG. 1C shows western blot results confirming the effects of Carbiferon (100 ng/ml) on the expression levels of death receptor-related genes.

FIG. 2A shows cell viability (bar graph; upper panel) and microscopic cell images (lower panel) according to the concentration and treatment time of Carbiferon. FIG. 2B shows qPCR results confirming the effects of Carbiferon (100 ng/ml) on the expression levels of death receptor-related genes. FIG. 2C shows western blot results confirming the effects of Carbiferon (100 ng/ml) on the expression levels of death receptor-related genes.

FIG. 3A shows western blot results of OVCAR-3 cell line, while FIG. 3B shows western blot results of HeLa cell line.

FIG. 4A shows the effect of cFLIP siRNA (a total of 10 nM) having mixed four types of nucleotide sequences on cell viability. FIG. 4B shows western blot results confirming the effect of the mixed cFLIP siRNA on caspase-8 levels.

FIG. 5A is a schematic diagram showing siRNA target sites for inhibiting the expression of both cFLIP long form ($cFLIP_L$) and short form ($cFLIP_S$). FIG. 5B shows nucleotide sequences of corresponding siRNA.

FIG. 6A shows western blot results showing cFLIP protein levels, which were observed after treatment with each type of siRNA (10 nM) for 48 hours. FIG. 6B shows qPCR results confirming the cFLIP mRNA level after treatment with each type of siRNA (20 nM) for 48 hours. The siRNAs marked by blue dotted lines represent primarily selected siRNAs. NC means negative control siRNA.

FIG. 7A shows cell viability in the treatment with corresponding siRNAs (10 nM) alone. FIG. 7B shows cell viability in the co-treatment with corresponding siRNAs (10 nM) and Carbiferon (100 ng/ml). The siRNAs marked by blue dotted lines represent secondarily selected siRNAs. NC means negative control siRNA.

FIG. 8A shows the results in SK-OV-3 cell line as ovarian cancer cells; FIG. 8B shows the results in SNU-216 cell line as gastric cancer cells; and FIG. 8C shows the results in NCI-N487 cell line as gastric cancer cells. NC means negative control siRNA. ACFP, which is an antibody-cytokine fusion protein, means a fusion protein in which Carbiferon is fused to a terminus of the heavy chain of Herceptin.

MODE FOR CARRYING OUT THE INVENTION

Hereinafter, the present invention will be described in detail.

However, the following examples are merely for illustrating the present invention and are not intended to limit the scope of the present invention.

Example 1

Differential Effects of Carbiferon According to IFNβ Resistance of Cancer Cells

Figure 1:
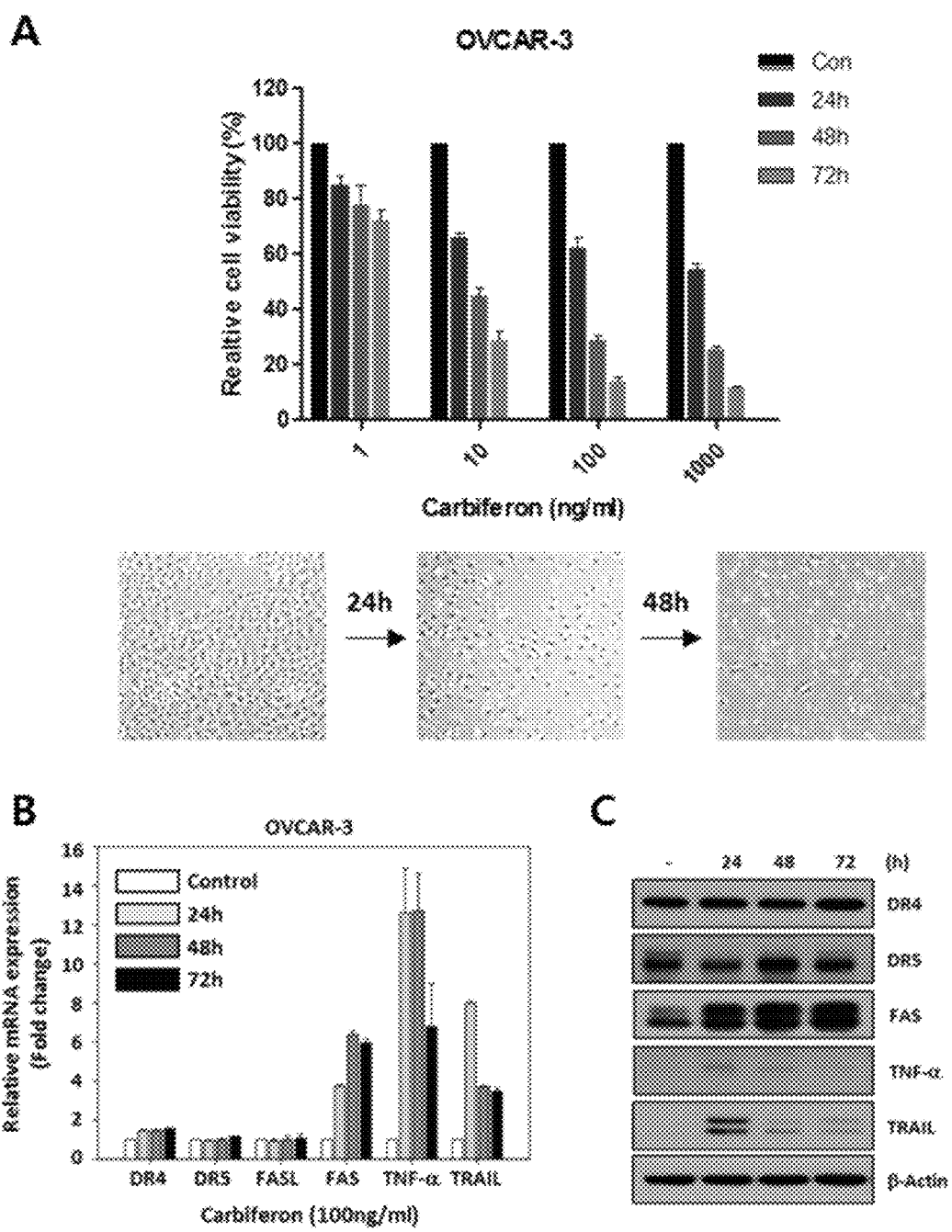
FIG. 1 shows test results confirming the effects of Carbiferon in OVCAR-3 cell line as IFNβ-responsive cancer cells.
Figure 2:
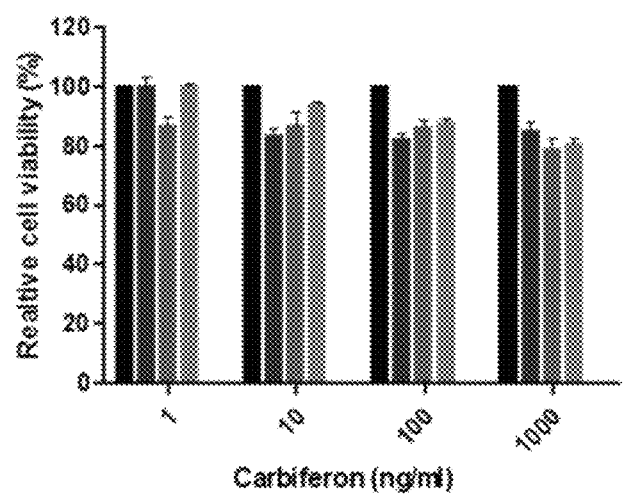
FIG. 2 shows test results confirming the effects of Carbiferon in HeLa cell line as IFNβ-nonreponsive cancer cells.
Figure 2:
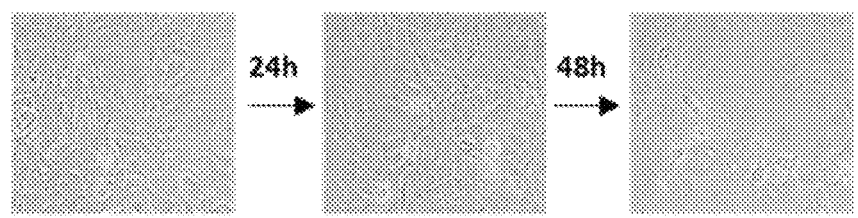
Figure 2:
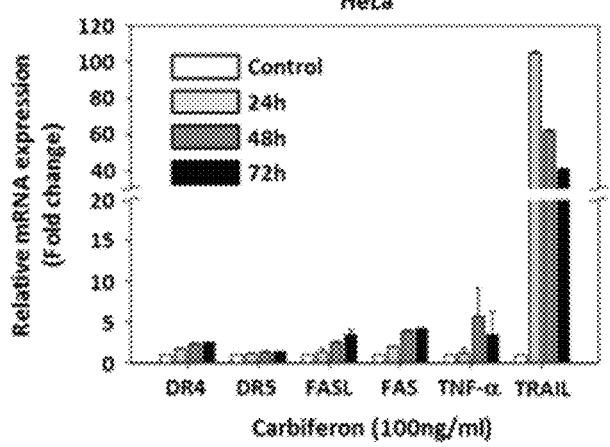
Figure 2:
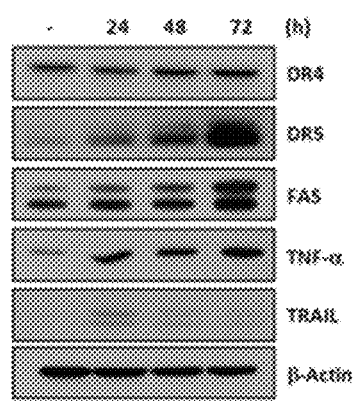

The anticancer effect of Carbiferon (R27T or the like) was compared in IFNβ-responsive cancer cells and IFNβ-nonresponsive resistant cancer cells (FIGS. 1 and 2).

In order to investigate the cytotoxicity of Carbiferon, OVCAR-3 cells ($1 \times 10^4$ cells/well) or HeLa cells ($5 \times 10^3$ cells/well) were dispensed in each well of a 96-well plate, and then incubated at 37.5° C. in a 5% $CO_2$ atmosphere for 24 hours. After 24 hours, the cell culture was removed, and the cells were treated with Carbiferon at concentrations of 10-1000 ng/ml, and then incubated for 24-72 hours. Thereafter, the culture was removed, followed by washing three times with PBS. WST reagent diluted to 1:10 was added at 100 μl per well, and then the cells were left at 37.5° C. in a 5% $CO_2$ atmosphere for 2 hours. The absorbance was measured at a wavelength of 430 nm.

TABLE 1

Primers used in qPCR

|  | Forward | Reverse |
| --- | --- | --- |
| DR4 | gggtccacaagaccttcaagt (SEQ ID NO: 22) | tgcagctgagctaggtacga (SEQ ID NO: 23) |
| DR5 | agaccttgtgctcgttgtc (SEQ ID NO: 24) | ttgttgggtgatcagagcag (SEQ ID NO: 25) |
| FASL | cagtccacccctgaaaaa (SEQ ID NO: 26) | ggaccttgagttggacttgc (SEQ ID NO: 27) |
| FAS | atggccaattctgccataag (SEQ ID NO: 28) | tgactgtgcagtccctagctt (SEQ ID NO: 29) |
| TNF-α | gacaagcctgtagcccatgt (SEQ ID NO: 30) | tctcagctccacgccatt (SEQ ID NO: 31) |
| Trail | cctcagagagtagcagctcaca (SEQ ID NO: 32) | cagagcctttcattcttgga (SEQ ID NO: 33) |

For the measurement of gene expression, OVCAR-3 or HeLa cells were treated with Carbiferon at a concentration of 100 ng/ml, and then incubated for 24-72 hours. Thereafter, the culture was removed, and PBS wash was carried out three times. The cells were collected, and then Trizol was utilized to extract RNA, on the basis of which cDNA was then synthesized. Thereafter, qPCR utilizing Taqman probe was performed using the synthesized cDNA as a template. Primer nucleotide sequences used in qPCR are shown in Table 1.

Figure 3:
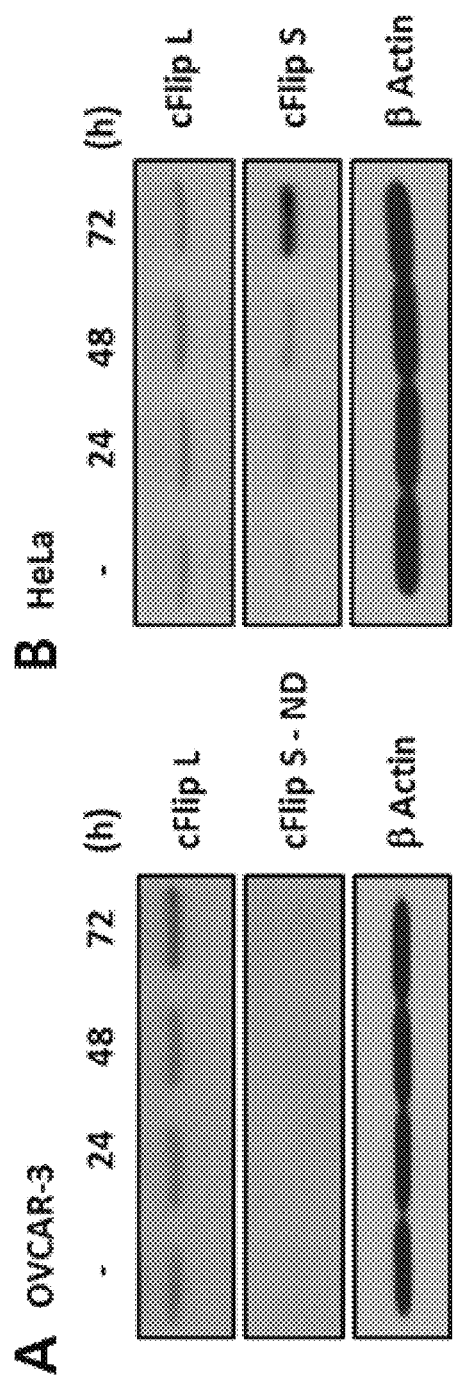
FIG. 3 shows test results confirming the changes in expression levels of cFLIP by Carbiferon (100 ng/ml) in IFNβ-responsive or -nonresponsive cancer cells.

In order to investigate the expression patterns of death receptor signaling molecules by Carbiferon, OVCAR-3 or HeLa cell line was treated with 100 ng/ml Carbiferon, and then incubated in the same manner as described above. The cell culture was washed three times with PBS, treated with 100 µl of RIPA buffer containing a protease inhibitor and a phosphatase inhibitor, and placed on ice for 30 minutes to lyse cells. The lysed cells were placed in a 1.5-mL tube, and centrifuged at 13,000 rpm at 4° C. Then, only the supernatant (lysate) was taken, and collected in a new tube. The concentrations of proteins of the lysate were quantified by BCA assay, and then 30 µg of the lysate was taken, mixed with 5× sample buffer, and boiled at 100° C. for 10 minutes to induce sufficient protein denaturation. The prepared sample, together with a marker, was loaded onto a 10% SDS-PAGE gel, and was allowed to flow out at 70 V for 30 minutes and 120 V for 1 hour. Thereafter, the gel was carefully separated, and placed on 3M paper, and then a polyvinylidene difluoride (PVDF) membrane was disposed thereon, and again covered with 3M paper. Thereafter, the membrane was immersed in 1× transfer buffer, followed by protein transfer at 100 V for 90 minutes. The membrane was blocked in tris-buffered saline-Tween 20 (TBS-T, 0.1% Tween 20) containing 5% BSA for 1 hour and 30 minutes, and then each antibody was prepared by dilution at 1:1000 in TBS-T. The membrane was immersed in the antibody diluted solution, followed by incubation with shaking at room temperature for 2 hours. After this procedure, the membrane was washed three times with TBS-T for 10 minutes, and a horseradish peroxidase (HRP)-conjugated secondary antibody was added thereto, followed by reaction for 1 hour. The membrane was again washed, treated with an enhanced chemiluminescence (ECL, Intron) reagent, and then developed on films. In FIG. 1C, FIG. 2C, and FIG. 3, Lane 1 represents a control, and Lanes 2, 3, and 4 represent 24 hour-, 48 hour-, and 72 hour-Carbiferon 100 ng/ml treatment groups, respectively.

As a result of investigating cell viability after OVCAR-3 cell line as IFNβ-responsive cancer cells was treated with Carbiferon as an IFNβ mutant at concentrations of 1, 10, 100, or 1000 ng/ml, and then incubated for 24-72 hours, it was observed that the cell viability of the OVCAR-3 cells significantly decreased dependent on the concentration of Carbiferon and with a longer incubation time (FIG. 1A). In addition, as a result of investigating the expression levels of DR4, DR5, FASL, FAS, TNF-α, and TRAIL involved in death receptor signaling, which is important in cell apoptosis, through qPCR (FIG. 1B) and western blot (FIG. 1C), their expression levels were significantly increased.

In contrast, as a result of investigating the effects of Carbiferon when HeLa cell line as IFNβ-nonresponsive and resistant cancer cells was incubated in the same manner, it was observed that the cell viability was not significantly changed even at the highest concentration (FIG. 2A), but the death receptor signaling-related genes showed increased expression even in the HeLa cell line (FIG. 2B and FIG. 2C).

Meanwhile, as a result of investigating the expression of cFLIP, which is a protein inhibiting cell apoptosis, in IFNβ-responsive OVCAR-3 cell line and IFNβ-nonresponsive HeLa cell line, it was observed that the level of the cFLIP proteins was increased only in HeLa cell line stimulated with Carbiferon (100 ng/ml) (FIG. 3). These results suggest that the inhibition of cFLIP protein expression may be used as a sensitizer for the treatment of an IFNβ-nonresponsive cancer disease.

Example 2

Effect of cFLIP Expression Inhibition on the Activity of Carbiferon

Figure 4:
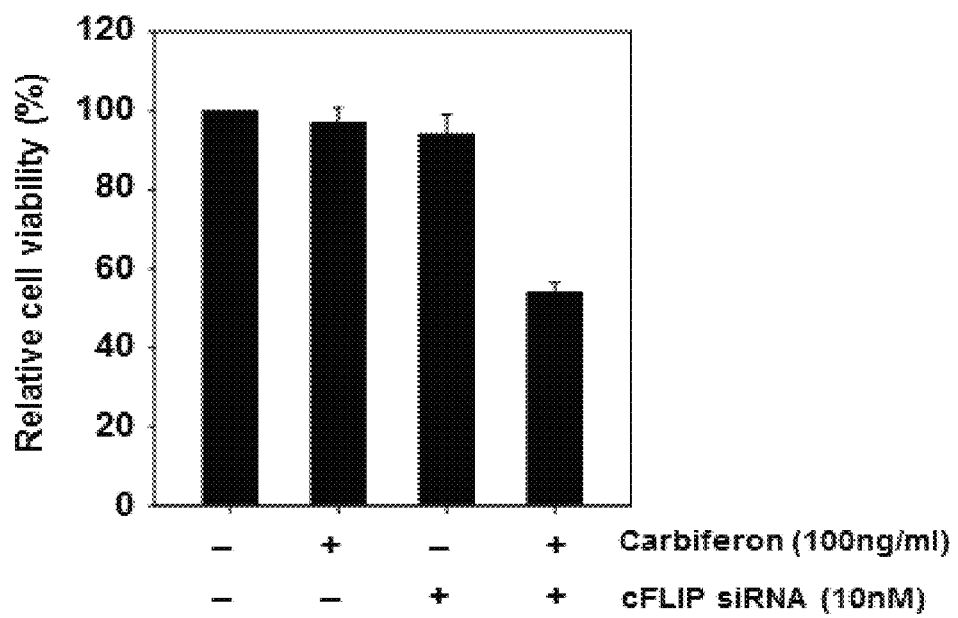
FIG. 4 shows test results confirming the effect of the inhibition of cFLIP gene expression on the anticancer effect of Carbiferon in HeLa cell line.
Figure 4:
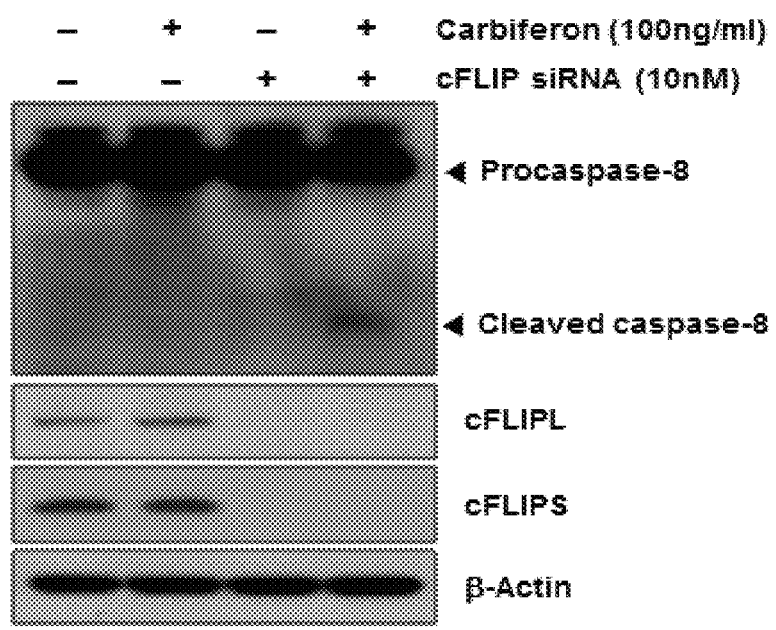

The effect of the inhibition of cFLIP protein expression on the anticancer effect of Carbiferon in cancer cells was investigated using cFLIP siRNA (FIG. 4).

In order to investigate the improvement in cytotoxic ability of Carbiferon by cFLIP inhibition, $1 \times 10^4$ cells/well of HeLa cells were dispensed in a 24-well plate, and incubated at 37.5° C. in a 5% $CO_2$ atmosphere for 24 hours. After 24 hours, the cell culture was removed, and then 10 nM cFLIP siRNA (Dharmacon, cat #LU-003772-00-0002) was mixed with Dharmafect transfection reagent, and the cells were treated with the mixture after the incubation at room temperature for 15 minutes. After 24-hour treatment, the culture was removed, and the cells were treated with 100 ng/ml of Carbiferon, and additionally incubated for 48 hours. Thereafter, the culture was removed, followed by washing three times with PBS, and then cell viability was measured (FIG. 4A) or protein expression was checked (FIG. 4B).

In order to measure cell viability, WST reagent was mixed with the culture at 1:10, and then each well was treated with the mixture, and incubated at 37.5° C. in a 5% $CO_2$ atmosphere for 2 hours. The absorbance was measured at a wavelength of 430 nm.

For western blot for investigating protein expression, each well was treated with 100 µl of RIPA buffer containing a protease inhibitor and a phosphatase inhibitor, and placed on ice for 30 minutes to lyse cells. The lysed cells were placed in a 1.5-mL tube, and centrifuged at 13,000 rpm at 4° C., and then only the supernatant (lysate) was taken, and collected in a new tube. The concentrations of proteins of the lysate were quantified by BCA assay, and then 30 µg of the lysate was taken, mixed with 5× sample buffer, and boiled at 100° C. for 10 minutes to induce sufficient protein denaturation. The prepared sample, together with a marker, was loaded onto a 10% SDS-PAGE gel, and was subjected to electrophoresis at 70 V for 30 minutes and 120 V for 1 hour. Thereafter, the gel was carefully separated, and placed on 3M paper, and then a polyvinylidene difluoride (PVDF) membrane was disposed thereon, and again covered with 3M paper. Thereafter, the membrane was immersed in 1× transfer buffer, followed by protein transfer at 100 V for 90 minutes. The membrane was blocked in tris-buffered saline-Tween 20 (TBS-T, 0.1% Tween 20) containing 5% BSA for 1 hour and 30 minutes, and then each antibody was prepared by dilution at 1:1000 in TBS-T. The membrane was immersed in the antibody diluted solution, followed by reaction with shaking at room temperature for 2 hours. After this procedure, the membrane was washed three times with TBS-T for 10 minutes, and a horseradish peroxidase (HRP)-conjugated secondary antibody was added thereto, followed by reaction at room temperature for 1 hour. The membrane was again washed, treated with an enhanced chemiluminescence (ECL, Intron) reagent, and then developed on films. In FIG. 4B, Lane 1 represents a control, Lane 2 represents a Carbiferon alone treatment group, Lane 3 represents siRNA alone treatment group, and Lane 4 represents a Carbiferon and cFLIP siRNA co-treatment group.

The IFNβ mutant, Carbiferon, activates death receptor signaling systems in cancer cells, resulting in causing cell apoptosis by caspase-3. In order to inhibit the expression of cFLIP protein, four types of cFLIP siRNA on the market (Dharmacon, cat #LU-003772-00-0002) were mixed, and HeLa cells were treated with the mixture. Then, cell viability was measured in the presence or absence of Carbiferon (FIG. 4A). It was confirmed through western blot that the expression of both long-form cFLIP and short-form cFLIP was almost completely inhibited by cFLIP siRNA (FIG. 4B, cFLIPL and cFLIPS). As a result, the cell viability in the treatment with only Carbiferon (100 ng/ml) or only cFLIP siRNA (10 nM) was insignificantly different from that of the control group, but the cell viability in the co-treatment with Carbiferon and cFLIP siRNA was reduced by about 50% compared with that of the control group. In addition, western blot results confirmed the presence of activated cleaved caspase-8, which is important in cell apoptosis, only in the co-treatment group with Carbiferon and cFLIP siRNA. The results above indicate that the inhibition of cFLIP expression by cFLIP siRNA can effectively promote cell apoptosis by Carbiferon in IFNβ-nonresponsive cells.

Example 3

Selection of cFLIP siRNA for Sensitizing IFNβ-Resistant Cancer Cells

An optimal siRNA for sensitizing cell apoptotic effects of IFNβ or Carbiferon in IFNβ-nonresponsive cancer cells was designed and selected.

Figure 5:
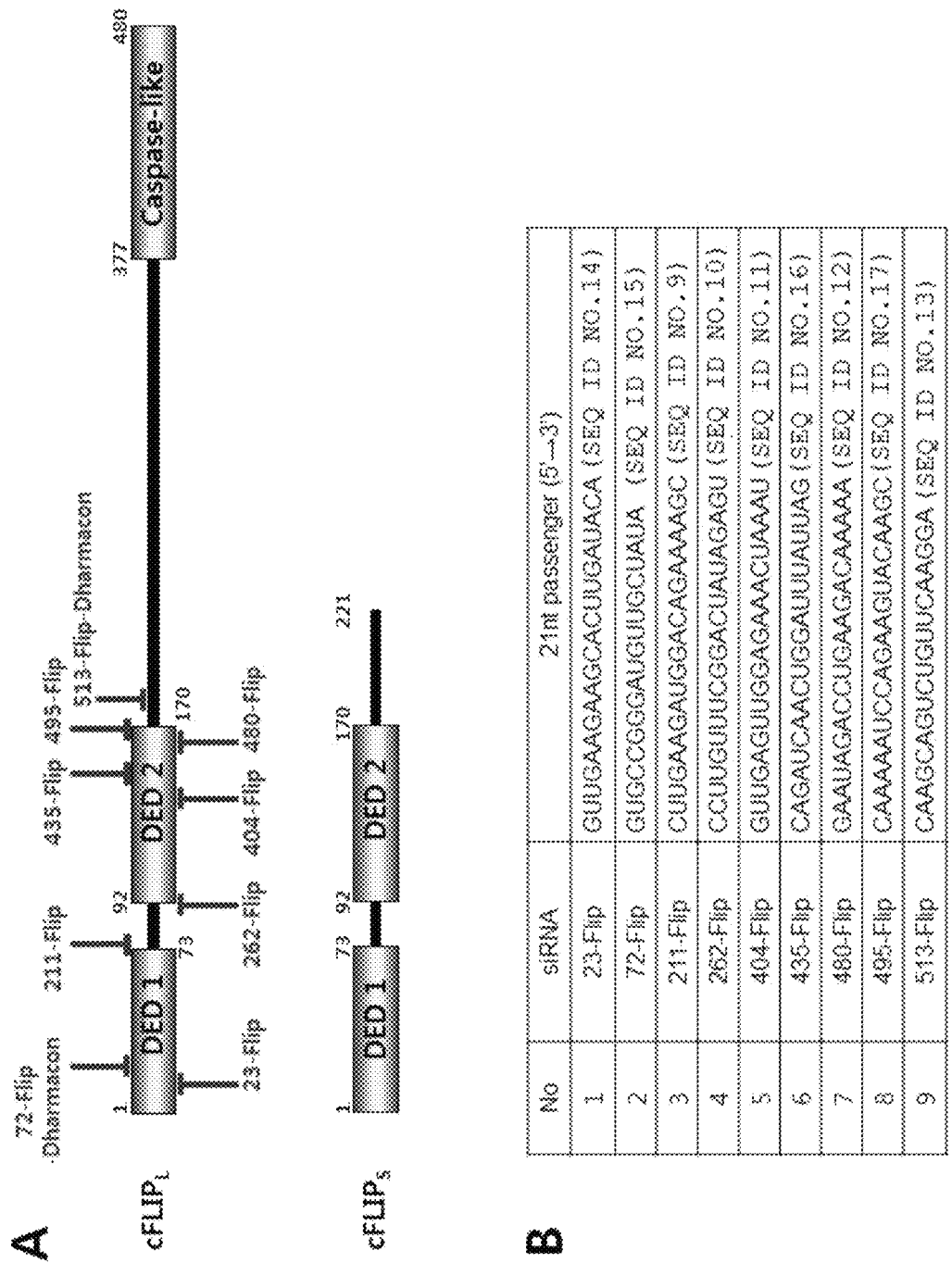
FIG. 5 shows a siRNA design for inhibiting the expression of cFLIP gene.

Since long-form cFLIP and short-form cFLIP execute the same functions with respect to cell apoptosis, siRNA capable of inhibiting the expression of both two types of cFLIP is most preferable, and therefore the locations and sequences of suitable target sequences of cFLIP were determined (FIG. 5). First, seven types of siRNA were selected using siDirect version 2.0 program, and two types of siRNA on the market were additionally included (Dharmacon).

Figure 6:
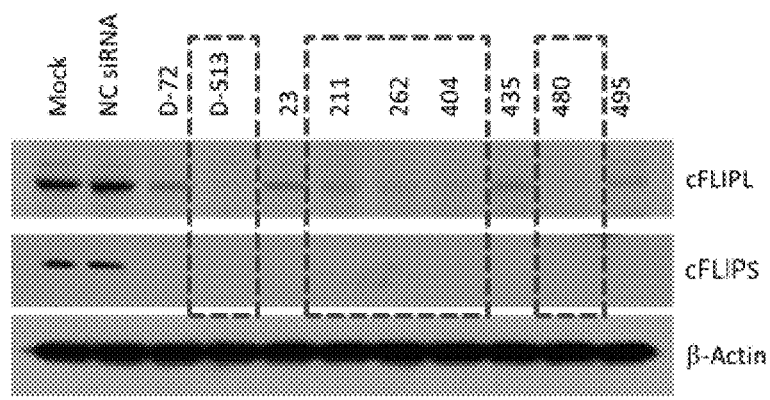
FIG. 6 shows test results confirming cFLIP siRNA expression inhibitory ability in HeLa cell line.
Figure 6:
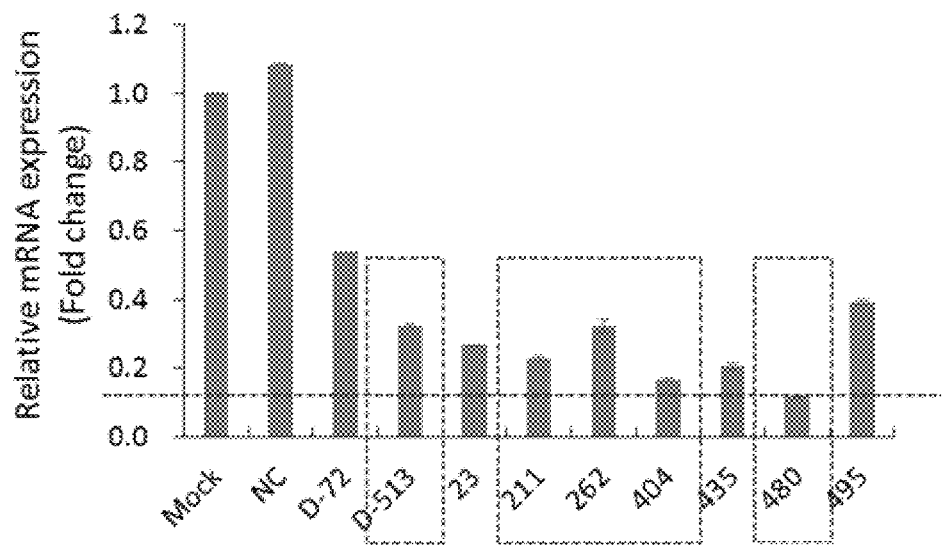

In order to investigate cFLIP inhibitory ability of the designed cFLIP siRNA, HeLa cells were dispensed, and incubated at 37.5° C. in a 5% $CO_2$ environment for 24 hours. After 24 hours, the cell culture was removed, and 10 nM siRNA was mixed with Dharmafect transfection reagent, and the cells were treated with the mixture after the incubation at room temperature for 15 minutes. After 48 hours, the culture was removed, and western blot was performed by the same method as in the foregoing example. In FIG. 6A, Lane 1 represents Mock, Lane 2 represents negative control siRNA (NC siRNA), and Lanes 3 to 11 represent designed cFLIP siRNA treatment groups. Trizol was utilized to extract RNA from the cells, which were obtained by transformation with 20 nM siRNA and incubation in the same manner, and then cDNA was synthesized on the basis of the extracted RNA. In addition, qPCR utilizing Taqman probe was performed using the synthesized cDNA as a template (FIG. 6B).

HeLa cell line as IFNβ-nonresponsive cells were treated with the selected siRNAs for 48 hours, and then protein levels of cFLIP long form ($cFLIP_L$) and cFLIP short form ($cFLIP_S$) were investigated by western blot (FIG. 6A). The $cFLIP_L$ and $cFLIP_S$ proteins were not detected in all of the cells treated with nine (9) types of siRNA as targets of analysis. In addition, it was observed that the cFLIP mRNA levels measured by qPCR were reduced by about 50% or more in the cells treated with siRNAs compared with the control group. The five types of siRNA, D-513, 211, 262, 404, and 480, which were confirmed to have excellent cFLIP expression inhibitory ability on the basis of qPCR and western blot results, were primarily selected.

Figure 7:
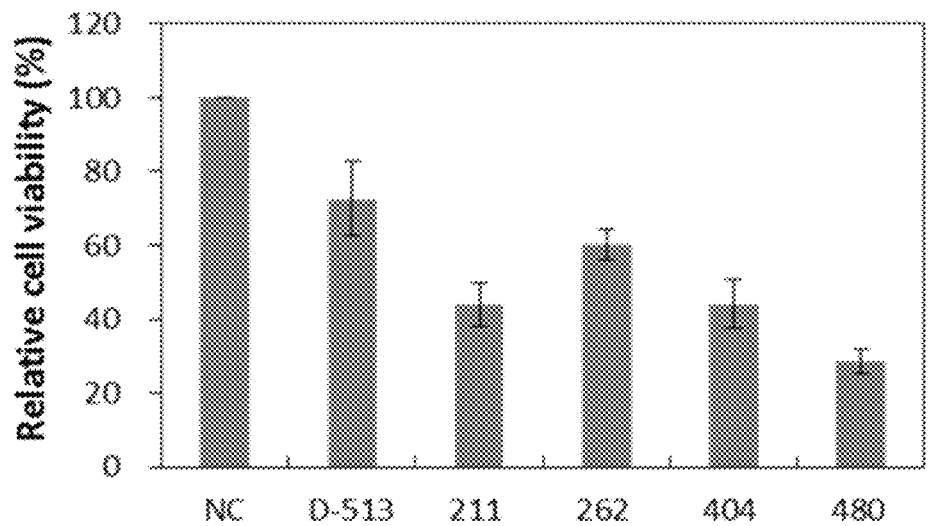
FIG. 7 shows test results confirming the effects of primarily selected siRNAs in HeLa cell line.
Figure 7:
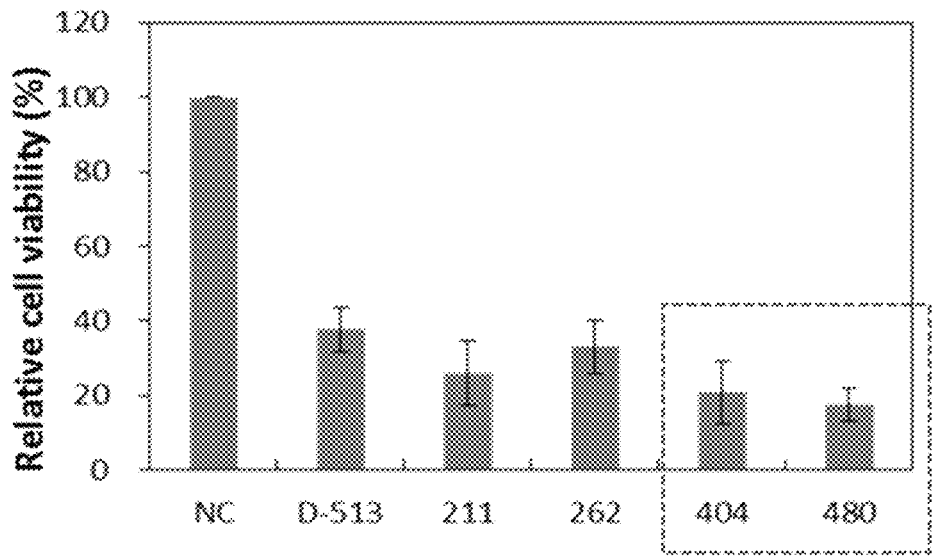

The effect of the primarily selected cFLIP siRNAs on cell apoptotic effects of Carbiferon was further investigated using HeLa cell line. First, in order to investigate the effect of each siRNA on cell apoptosis, the cells were treated with each siRNA alone without Carbiferon, and cell viability was measured in the same manner as in the foregoing example (FIG. 7A). HeLa cells were inoculated on a plate, treated with siRNA (final concentration: 10 nM) after 24 hours, and subjected to WST assay after additional 24 hours. As a result, it was observed that cell viability was decreased, and thus even siRNA alone showed cytotoxicity, that is, a cell apoptosis inducing effect.

Next, the effect of co-treatment with cFLIP siRNA and Carbiferon was investigated (FIG. 7B). HeLa cell line was treated with siRNA (final concentration: 10 nM) 24 hours after inoculation, and treated with Carbiferon (100 ng/ml) after additional 24 hours, and then cell viability after 24 hours was measured. It was observed that the co-treatment with Carbiferon and siRNA had a synergistic effect in lowering the cell viability of the HeLa cell line compared with the treatment with only siRNA. Out of the siRNAs analyzed for the effects of the co-treatment with Carbiferon, 404 cFLIP siRNA and 480 cFLIP siRNA, which had the best effects, were secondarily selected.

Example 4

Figure 8:
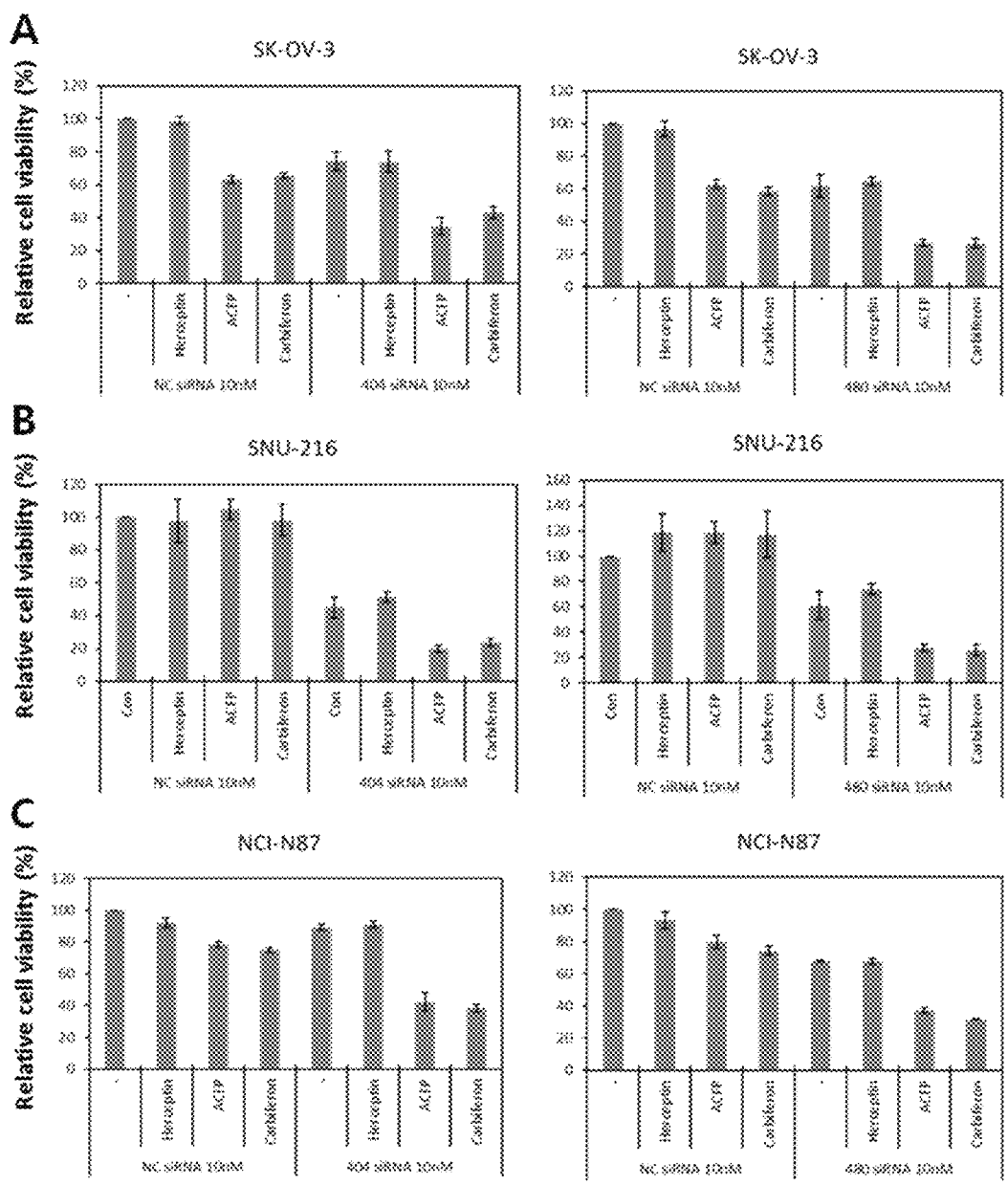
FIG. 8 shows test results confirming the effects of administration of secondarily selected siRNAs (10 nM) alone or together with an anticancer drug on cell viability in various cancer cell lines.

Effect of Co-Treatment with cFLIP siRNA and Carbiferon in Various Cancer Cell Lines The sensitization effect of the finally selected 404 cFLIP siRNA and 480 cFLIP siRNA on IFNβ-nonresponsive cancer cells was investigated using various cancer cell lines (FIG. 8).

In order to investigate cell apoptotic ability by co-treatment of the selected cFLIP siRNAs together and Carbiferon or ACFP, SK-OV-3, SNU-216, and NCI-N87 cells were dispensed at $1 \times 10^4$ cells/well in a 24-well plate, and incubated at 37.5° C. in a 5% $CO_2$ environment for 24 hours. ACFP is a fusion protein in which Carbiferon (R27T) is fused to a terminus of the heavy chain of Herceptin. After 24 hours, the cell culture was removed, and 10 nM siRNA was mixed with Dharmafect transfection reagent, and the cells were treated with the mixture after the incubation at room temperature for 15 minutes. After 24-hour treatment, the culture was removed, and the cells were treated with 100 ng/ml of Carbiferon, ACFP, and Herceptin and additionally incubated for 48 hours. Thereafter, the culture was removed, followed by washing three times with PBS. Then, WST reagent was mixed with the culture at 1:10, and each well were treated with the mixture, and incubated at 37.5° C. in a 5% $CO_2$ atmosphere for 2 hours. The absorbance was measured at a wavelength of 430 nm. The cell lines used in the present example were confirmed that they do not respond to IFNβ at all (SNU-216) or have very low sensitivity to IFNβ (SK-OV-3 or NCI-N87), in comparison with cells normally responding to IFNβ (Data not shown).

The effects of cFLIP siRNAs in SK-OV-3 cell line as ovarian cancer cells (FIG. 8A), SNU-216 cell line as gastric cancer cells (FIG. 8B), and NCI-N87 cell line as gastric cancer cells (FIG. 8C) were investigated by measuring cell viability. In cases where the cells were not treated with siRNA, ACFP, which is a fusion protein in which Carbiferon and Herceptin are bound, was more effective in reducing cancer cell viability than Herceptin alone. Furthermore, it was observed that the cell apoptotic effects of ACFP and Carbiferon were further enhanced when the cells were treated with cFLIP siRNA and ACPF or Carbiferon.

INDUSTRIAL APPLICATION

As set forth above, the composition of the present invention can be favorably used to develop a novel mechanism of anticancer drug or adjuvant, which attains an effective sensitization and treatment by lowering the expression levels of cFLIP proteins in cancers showing resistance to interferon-beta or cancers having resistance to interferon-beta, thereby effectively sensitizing cancer.

The invention claimed is:

1. A method for treating an interferon-beta-resistant cancer disease, comprising administering to a subject in need thereof an effective amount of:
   (a) siRNA which binds to mRNA of cFLIP gene in a complementary manner; and
   (b) a human interferon-beta mutant which comprises a glycine-asparagine-isoleucine-threonine-valine (GNITV) sequence at the C-terminus or in which threonine or serine is substituted for arginine at the 27th amino acid, in a wild-type human interferon-beta amino acid sequence defined by SEQ ID NO: 1,
   wherein the interferon-beta mutant comprises any one amino acid sequence selected from the group consisting of SEQ ID NO: 2 to SEQ ID NO: 6 and SEQ ID NO: 18 to SEQ ID NO: 21,
   wherein the siRNA comprises any one nucleotide sequence selected from the group consisting of SEQ ID NO: 9 to SEQ ID NO: 13.

2. The method of claim 1, wherein the siRNA and human interferon-beta mutant are administered simultaneously.

3. The method of claim 1, wherein the siRNA and human interferon-beta mutant are administered sequentially.

4. The method of claim 1, wherein the cancer disease is not ovarian or gastric cancer.

5. The method of claim 4, wherein the cancer disease is selected from the group consisting of breast cancer, lung cancer, colon cancer, anal cancer, astrocytoma, leukemia, lymphoma, head and neck cancer, liver cancer, testicular cancer, cervical cancer, sarcoma, hemangioma, esophageal cancer, eye cancer, laryngeal cancer, oral cancer, mesothelioma, myeloma, oral cavity cancer, rectal cancer, throat cancer, bladder cancer, uterine cancer, prostate cancer, large intestine cancer, pancreatic cancer, renal cancer, skin cancer, basal cell carcinoma, melanoma, squamous cell carcinoma, oral squamous cell carcinoma, colorectal cancer, glioblastoma, endometrial cancer, and malignant glioma.

6. A method for sensitizing interferon-beta-resistant cancer cells, comprising administering to the cells:
   a siRNA which binds to mRNA of cFLIP gene in a complementary manner, wherein the siRNA comprises any one nucleotide sequence selected from the group consisting of SEQ ID NO: 9 to SEQ ID NO: 13, and
   an interferon-beta mutant which comprises any one amino acid sequence selected from the group consisting of SEQ ID NO: 2 to SEQ ID NO: 6 and SEQ ID NO: 18 to SEQ ID NO: 21.

7. The method of claim 6, wherein the siRNA and human interferon-beta mutant are administered simultaneously.

8. The method of claim 6, wherein the siRNA and human interferon-beta mutant are administered sequentially.

9. The method of claim 6, wherein the cancer disease is not ovarian or gastric cancer.

10. The method of claim 9, wherein the cancer disease is selected from the group consisting of breast cancer, lung cancer, colon cancer, anal cancer, astrocytoma, leukemia, lymphoma, head and neck cancer, liver cancer, testicular cancer, cervical cancer, sarcoma, hemangioma, esophageal cancer, eye cancer, laryngeal cancer, oral cancer, mesothelioma, myeloma, oral cavity cancer, rectal cancer, throat cancer, bladder cancer, uterine cancer, prostate cancer, large intestine cancer, pancreatic cancer, renal cancer, skin cancer, basal cell carcinoma, melanoma, squamous cell carcinoma, oral squamous cell carcinoma, colorectal cancer, glioblastoma, endometrial cancer, and malignant glioma.

* * * * *